US012673977B2

(12) United States Patent
Marshall et al.

(10) Patent No.: US 12,673,977 B2
(45) Date of Patent: Jul. 7, 2026

(54) HETEROLOGOUS PROTEINS WITH AXONEMAL PROTEINS

(71) Applicants: THE REGENTS OF THE UNIVERSITY OF CALIFORNIA, Oakland, CA (US); THE TEXAS A&M UNIVERSITY SYSTEM, College Station, TX (US)

(72) Inventors: Wallace F. Marshall, Oakland, CA (US); Hongmin Qin, College Station, CA (US)

(73) Assignees: THE REGENTS OF THE UNIVERSITY OF CALIFORNIA, Oakland, CA (US); THE TEXAS A&M UNIVERSITY SYSTEM, College Station, TX (US)

( * ) Notice: Subject to any disclaimer, the term of this patent is extended or adjusted under 35 U.S.C. 154(b) by 676 days.

(21) Appl. No.: 17/759,918

(22) PCT Filed: Feb. 3, 2021

(86) PCT No.: PCT/US2021/016482
§ 371 (c)(1),
(2) Date: Aug. 1, 2022

(87) PCT Pub. No.: WO2021/158708
PCT Pub. Date: Aug. 12, 2021

(65) Prior Publication Data
US 2023/0340036 A1 Oct. 26, 2023

Related U.S. Application Data

(60) Provisional application No. 62/969,509, filed on Feb. 3, 2020.

(51) Int. Cl.
*C07K 14/405* (2006.01)
*C12N 9/02* (2006.01)
(Continued)

(52) U.S. Cl.
CPC .......... *C07K 14/405* (2013.01); *C12N 9/0006* (2013.01); *C12N 9/0022* (2013.01);
(Continued)

(58) Field of Classification Search
CPC .............. C07K 14/405; C07K 2319/50; C12N 9/0006; C12N 9/0036; C12N 9/86;
(Continued)

(56) References Cited

U.S. PATENT DOCUMENTS

| | | | |
|---|---|---|---|
| 6,506,595 B2 * | 1/2003 | Sato ....................... | C07K 14/62 |
| | | | 435/325 |
| 2010/0267130 A1 | 10/2010 | Witman et al. | |

(Continued)

FOREIGN PATENT DOCUMENTS

WO WO-2017165788 A1 * 9/2017 ......... G01N 21/6428

OTHER PUBLICATIONS

Blomberg, Rebecca, et al. "Precision is essential for efficient catalysis in an evolved Kemp eliminase." Nature 503.7476 (2013): 418-421. doi.org/10.1038/nature 12623 (Year: 2013).*
Tran et al. "Production of unique immunotoxin cancer therapeutics in algal chloroplasts." PNAS. 110.1 (2013): E15-E22. doi.org/10.1073/pnas.1214638110 (Year: 2013).*
(Continued)

*Primary Examiner* — Anand U Desai
*Assistant Examiner* — Andrew T Moehlman
(74) *Attorney, Agent, or Firm* — Mintz Levin Cohn Ferris Glovsky and Popeo PC

(57) ABSTRACT

Provided herein are compositions and methods for the production of heterologous proteins in a cell including axonemes. The cells include a nucleic acid encoding a fusion protein expressed in the axoneme. The fusion protein includes an axonemal protein linked to a heterologous protein, and the fusion protein provides axonemal function to the cell.

7 Claims, 20 Drawing Sheets

(51) Int. Cl.

| | |
|---|---|
| *C12N 9/04* | (2006.01) |
| *C12N 9/06* | (2006.01) |
| *C12N 9/86* | (2006.01) |
| *C12N 9/88* | (2006.01) |
| *C12N 15/79* | (2006.01) |

(52) U.S. Cl.
CPC .............. *C12N 9/0036* (2013.01); *C12N 9/86* (2013.01); *C12N 9/88* (2013.01); *C12N 15/79* (2013.01); *C07K 2319/50* (2013.01); *C07K 2319/735* (2013.01); *C12Y 101/01065* (2013.01); *C12Y 104/03004* (2013.01); *C12Y 106/03001* (2013.01); *C12Y 305/02006* (2013.01); *C12Y 401/01048* (2013.01)

(58) Field of Classification Search
CPC ............ C12N 15/79; C12Y 104/03004; C12Y 106/03001; C12Y 305/02006
See application file for complete search history.

(56) References Cited

U.S. PATENT DOCUMENTS

| | | | | |
|---|---|---|---|---|
| 2014/0030771 A1* | 1/2014 | Yu | ........................... | C08L 91/00 |
| | | | | 435/134 |
| 2018/0203017 A1 | 7/2018 | Ting et al. | | |

OTHER PUBLICATIONS

Azuma, Yusuke et al. "Quantitative Packaging of Active Enzymes into a Protein Cage." Angewandte Chemie (International ed. in English) vol. 55,4 (2016): 1531-4. doi:10.1002/anie.201508414 (Year: 2016).*

Yanagisawa, H.A. et al. (May 2014, e-published Feb. 26, 2014). "FAP20 is an inner junction protein of doublet microtubules essential for both the planar asymmetrical waveform and stability of flagella in Chlamydomonas," Mol Biol Cell 25(9):1472-1483. (Year: 2014).*

Ishikawa et al. Mar. 2019, "Cell-based biosynthesis of linear protein nanoarrays". In Reporters, Markers, Dyes, Nanoparticles, and Molecular Probes for Biomedical Applications XI, Proceedings of the SPIE, vol. 10893, pp. 15-30. doi.org/10.1117/12.2510226 (Year: 2019).*

Gregoretti, I.V. et al. (2006). "Insights into cytoskeletal behavior from computational modeling of dynamic microtubules in a cell-like environment," *J Cell Sci* 119(Pt 22):4781-4788.

International Search Report mailed on Jun. 8, 2021, for PCT Application No. PCT/US2021/016482, filed Feb. 3, 2021, 4 pages.

Written Opinion mailed on Jun. 8, 2021, for PCT Application No. PCT/US2021/016482, filed Feb. 3, 2021, 7 pages.

Yanagisawa, H.A. et al. (May 2014, e-published Feb. 26, 2014). "FAP20 is an inner junction protein of doublet microtubules essential for both the planar asymmetrical waveform and stability of flagella in Chlamydomonas," *Mol Biol Cell* 25(9):1472-1483.

* cited by examiner

The Ciliary/Flagellar 9 + 2 Axoneme

Fused target protein

HETEROLOGOUS PROTEINS WITH AXONEMAL PROTEINS

CROSS-REFERENCE TO RELATED APPLICATIONS

This application is a U.S. National Phase Application of International Patent Application No. PCT/US2021/016482, filed Feb. 3, 2021, which claims the benefit of U.S. Provisional Application No. 62/969,509, filed Feb. 3, 2020, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant no. R01 GM097017 awarded by The National Institutes of Health and grant no. DBI1548297 awarded by The National Science Foundation. The government has certain rights in the invention.

BACKGROUND

Protein expression is a core methodology in biotechnology, which allows the power of biological enzymes to be harnessed to drive a wide range of chemical reactions. A recent innovation in protein engineering and biotechnology has focused on encapsulating enzymes into nanoparticles. Incorporation of proteins into self-assembled nanoparticles confers several advantages compared to soluble protein or protein adsorbed onto beads. First, the quantity of protein per particle can be highly reproducible owing to the self-assembly process. Second, proteins that are inherently insoluble can be rendered more tractable by incorporation into a particle along with the self-assembly scaffold. Third, the local concentration of protein can be extremely high within a particle, potentially allowing channeling of reaction products if enzymes responsible for sequential steps are included together in the same particle. This channeling can lead to more efficient overall reactions as well as restricting the release of potentially toxic intermediates. Naturally occurring enzymatic nanoparticles include the carboxysome responsible for carbon fixation in some bacteria and the polyketide synthase particles. The self-assembly of such particles can be harnessed to build synthetic nanoparticles containing a virtually limitless range of possible enzymes or other proteins of value. Examples of self-assembling nanoparticles capable of encapsulating fixed quantities of enzymes are nanoreactors based on bacteriophage MS2 capsid proteins and the non-viral lumazine synthase protein. Both proteins assemble into polyhedral shapes of defined size, creating a capsule with a lumen into which suitably tagged enzymes can be docked during particle assembly via protein-protein interactions.

One limitation of self-assembled nanoparticles is the total quantity of protein that can be incorporated. This is because the polyhedral geometry of the particle produces as strict size limitation. For example, lumazine synthase based nanoparticles can accommodate a maximum of 45 guest proteins inside their lumen. One can easily imagine applications in which an order of magnitude more copies of an enzyme might be desirable in a single particle. Fundamentally, the limiting factor with polyhedral nanoparticles is that the scaffold proteins assemble a closed surface which necessarily encapsulates a limited luminal volume. Linear protein arrays present one possible alternative structure in which size, and therefore the quantity of incorporated protein, could be much greater. There are many naturally occurring proteins that self-organize into linear arrays. Examples include cytoskeletal filaments such as actin and tubulin but also enzyme filaments such as glutamate synthase, CTP synthase, and the eIF2/2B complex. While self assembling filaments offer a way to increase protein content, they suffer from a much higher variability in total quantity. A population of self assembling linear polymers is predicted to show an exponential distribution of lengths, a prediction that has been confirmed through analysis of length distribution of actin and other polymers assembled in vitro. Constraining the polymerization to the interior of a cell can narrow the length distribution somewhat, since not only is the long tail of the distribution clipped due to the constraint of cell diameter, the extra monomer made available by loss of the extra long polymers can be used to increase the length of the short ones. Nevertheless, intracellular polymers still show wide length distributions of at least several fold, making them non-ideal as nanoarrays. (See, for example, Refs. 1-9).

In order for linear protein arrays to become viable as protein carrier arrays, some method is required to constrain length variation. Many prokaryotic and viral structures, such as bacteriophage tails and bacterial injectisomes are linear protein arrays whose length is tightly regulated by means of molecular "rulers", large proteins whose total length matches the length of the assembling structure. The ruler protein aligns alongside the growing array (phage tail or injectisome) and allows the growing end to continue growing. Once the array becomes longer than the ruler, further growth is arrested, for example by binding of a capping protein. Such molecular ruler based systems are limited in their maximum length by the maximum protein size, such that typical length scales end up being in the hundred-nanometer range. A second limitation of ruler-based length control systems is that if one wanted to produce a longer or shorter array, it would be necessary to design and test a new ruler protein, thus creating a potentially difficult protein engineering challenge. In some cases, it has been possible to insert repeated sequences into the ruler to make a longer or shorter ruler, but even so this requires design of a new protein construct for any desired length. (See, for example, Refs. 10-11). Provided herein are solutions to these and other problems in the art.

BRIEF SUMMARY OF THE INVENTION

In an aspect, provided herein is an axoneme-containing cell including a nucleic acid encoding a fusion protein. The fusion protein includes an axonemal protein linked to a heterologous protein, and the fusion protein provides axonemal function to the cell.

In an aspect, provided herein is an algal cell including a nucleic acid encoding a fusion protein, where the fusion protein includes an axonemal protein linked to a heterologous protein through an enzyme cleavable linker, and where the fusion protein provides axonemal function to the algal cell.

In an aspect, provided herein is a plurality of algal cells where each algal cell includes a nucleic acid encoding a fusion protein, where the fusion protein includes an axonemal protein linked to a heterologous protein through an enzyme cleavable linker, and where the fusion protein provides axonemal function to the algal cell.

In an aspect, provided herein is a recombinant protein including an algal axonemal protein and a heterologous protein. The axonemal protein is linked to the heterologous protein through an enzyme cleavable linker and the recombinant protein provides axonemal function to the algal cell.

In an aspect, provided herein is an isolated algal *flagella* that includes a flagellar membrane encompassing an axoneme, where the axoneme includes a fusion protein. The fusion protein includes an algal axonemal protein linked to a heterologous protein, and where the fusion protein provides axonemal function to the algal cell.

In an aspect, provided herein is an isolated axoneme that includes a fusion protein, where the fusion protein includes an algal axonemal protein linked to a heterologous protein, and where the fusion protein provides axonemal function to the algal cell.

In an aspect, provided herein is a plurality of axonemes where each of the plurality of axonemes includes a fusion protein. The fusion protein includes an algal axonemal protein linked to a heterologous protein, and the fusion protein provides axonemal function to the algal cell.

In an aspect, provided herein is a method of isolating a heterologous protein including expressing a fusion protein in an axoneme of a cell where the fusion protein includes an axonemal protein linked to a heterologous protein through a cleavable linker; separating the fusion protein from the *flagella*; and contacting the fusion protein with an enzyme thereby isolating said heterologous protein.

In an aspect, provided herein is a method of isolating a heterologous protein including expressing a fusion protein in an algal *flagella* of an algal cell where the fusion protein includes an algal axonemal protein linked to a heterologous protein through a cleavable linker; separating the fusion protein from the algal *flagella*; and contacting the fusion protein with an enzyme thereby isolating said heterologous protein.

BRIEF DESCRIPTION OF THE DRAWINGS

FIG. 1A is a simplified three-dimensional representation of a cilia or *flagella* axoneme.

FIG. 1B is a pictorial of an axoneme cross section and longitudinal view, showing location of IFT20, RSP3, and FAP20 in their respective complexes. FIG. 1C is a detailed three-dimensional representation of ciliary or flagellar axoneme.

FIG. 2A is a pictorial of a DMT showing the radial spoke (RS), the outer dynein arms (ODAs), and the inner dynein arms (IDAs). FIG. 2B is a pictorial of a single DMT tagged with different fusion proteins (cross-section view of a DMT; upper drawing), and a cartoon of a microtubule with different fusion proteins (side view of a DMT; bottom drawing).

FIG. 3A is a diagram of constructs showing GFP is fused to the protein. FIG. 3B are microscopy images of *Chlamydomonas* cell expressing GFP-tagged fusion constructs with IFT, RSP3, and FAP20. Scale bar for FIG. 3B: 10 μm.

FIG. 4A is a diagram showing steps of the image analysis algorithm used for the automatized identification of *flagella* from confocal images. FIG. 4B is an illustrative example of confocal image processed by the algorithm of FIG. 4A, showing segmentation of the *flagella*. FIG. 4C is a graph showing total GFP intensity versus flagellar length for three constructs, IFT20, RSP3, and FAP20, from confocal images after being processed by the algorithm of FIG. 4A.

FIG. 5A shows the workflow of flagellar isolation protocol followed by demembranation using the detergent NP-40 to produce axonemes. Storage of both types of particles can then be accomplished by freezing in liquid nitrogen and storing at −80 C. Panel i of FIG. 5B shows an image of detached *flagella* following pH shock and purification by centrifugation. Panel ii of FIG. 5B shows an image of axonemes obtained by demembranating the purified *flagella* with NP-40. Panels iii and iv of FIG. 5B show images of *flagella* (panel iii) and axonemes (panel iv) after freezing and thawing. Scale bar for panels i-iv: 10 μm.

FIG. 7A is a diagram showing a modified construct that comprises a TEV protease cleavage site, and FAP20 and GFP sequences. FIG. 7B show fluorescent microscopy images in which three examples each of untreated versus protease treated axonemes, in all cases fixed and stained to detect acetylated tubulin and GFP. The granular appearance of the GFP signal compared to earlier images is an artifact of methanol fixation required to image acetylated tubulin. Reduced GFP fluorescence in axonemes treated with TEV protease demonstrates release of most of the GFP domain from the fusion construct. Scale bar for FIG. 7B: 5 μm.

FIG. 8A is a diagram showing a modified construct that comprises a TEV protease cleavage site, and rsp3 and Bla sequences. FIG. 8B is a bar graph showing the construct of FIG. 8A in cells.

FIG. 9A is a diagram showing the construct of pBS-FAP20-GFP and pKF-RSP3-FP modified to express the fusion proteins of FAP20/RSP3 and the target protein. The fusion proteins were connected by a TEV-linker. The EcoRV-linker and GFP gene were deleted in both of the original constructs of pBS-FAP20-GFP and pKF-RSP3-GFP. In addition, the C-terminal 140 amino acids of RSP3 were deleted as well in the pKF-RSP3-GFP construct, and then replaced with a TEV-linker and the target gene. FIG. 9B is a diagram showing the schematic structure of *flagella* axoneme and the expression of the fusion proteins. The target protein is fused with an axoneme protein, such as FAP20 and RSP3. The axoneme protein is serving as an adaptor to transport and locate the target protein on to the axoneme and form a protein array in a high density and periodic manner.

FIG. 10A shows microscopy pictures of *Chlamydomonas* strains cc125 (wild type), FAP20-Bla and RSP3-Bla. These strains were cultured in the 4 L bubbly system. Cells were collected for *flagella* isolation when the concentration reached $10^6$ cells/ml. Original *flagella* were detached from the cell body by lowering pH to 4.5 transiently then bringing back to pH 7.0. The *flagella* and cell bodies can be separated easily by gently centrifuging at 2000 rpm. The purified *flagella* and cell bodies were suspended and cultured in HEPES buffer to regenerate *flagella*. Then the regenerated *flagella* were collected in the same way. The pictures show purified *flagella* under 100× of a light microscope, after regeneration. Scale bar equals 10 μm. FIG. 10B is a bar graph showing statistical results of the flagellar length in each of the strains after each step of flagellar regeneration. The error bars show the *flagella* length deviation. About 60 *flagella* were measured for each of the samples. Bla is Beta-lactamase.

DETAILED DESCRIPTION

I. Definitions

Figure 1A:
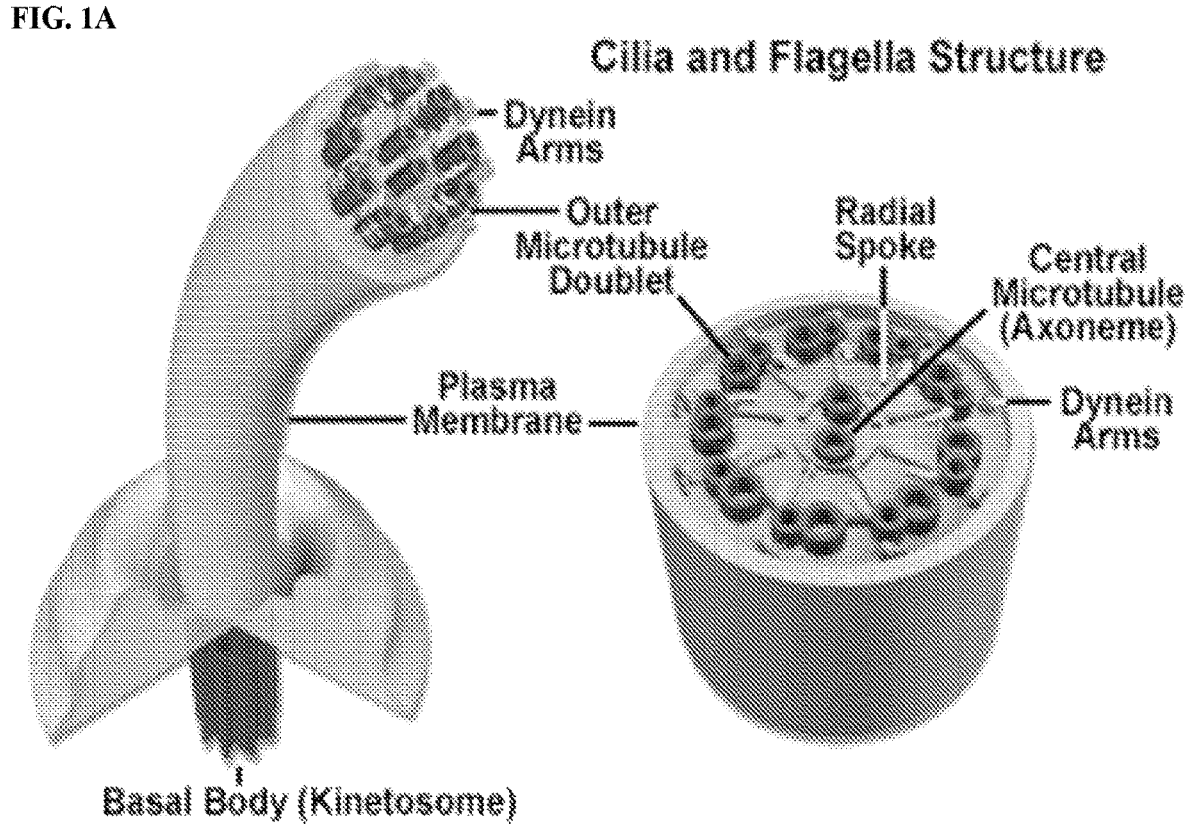
FIGS. 1A-1C present different drawings and representations of axonemes in cilia or *flagella*.

Before the present invention is further described, it is to be understood that this invention is not strictly limited to particular embodiments described, and as such may of course vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. It should further be understood that as used herein, the term "a" entity or "an" entity refers to one or more of that entity. For example, a nucleic acid molecule refers to one or more nucleic acid molecules. As such, the terms "a", "an", "one or more" and "at least one" can be used interchangeably. Similarly the terms "comprising", "including" and "having" can be used interchangeably.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

As used herein, the terms "specifically (or selectively) binds" or "specifically (or selectively) reactive with." when referring to a protein or peptide, are used in accordance with their plain ordinary meanings and refer to a binding reaction that is determinative of the presence of the protein, often in a heterogeneous population of proteins and other biologics.

As used herein, the terms "identical" or percent "identity." are used in accordance with their plain ordinary meanings and in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, the terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

"Nucleic acid" refers to nucleotides (e.g., deoxyribonucleotides or ribonucleotides) and polymers thereof in either single-, double- or multiple-stranded form, or complements thereof; or nucleosides (e.g., deoxyribonucleosides or ribonucleosides). In embodiments, "nucleic acid" does not include nucleosides. The terms "polynucleotide." "oligonucleotide." "oligo" or the like refer, in the usual and customary sense, to a linear sequence of nucleotides. The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

For specific proteins described herein, the named protein includes any of the protein's naturally occurring forms, variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

As used herein, the terms "Tobacco Etch Virus protease cleavage site", "Tobacco Etch Virus (TEV) protease cleavage site" and "TEV protease cleavage site" refer to an amino acid sequence that is recognized and cleaved by the Tobacco Etch Virus (TEV) protease (also known as Tobacco Etch Virus nuclear-inclusion-a endopeptidase). In embodiments, the TEV protease is a cysteine protease that recognizes the amino-acid sequence Glu-Asn-Leu-Tyr-Phe-Gln-(Gly/Ser) and cleaves between the Gln and Gly/Ser residues. The TEV protease is a member of the Proteases of mixed nucleophile, superfamily A (PA clan) of chymotrypsin-like proteases.

As used herein, the term "gene" refers to a segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The term "gene" also encompasses the coding regions of a structural gene and includes untranslated sequences located adjacent to the coding region on either or both of the 5' and 3' ends, and intervening untranslated regions, such that the term "gene" corresponds to the length of the entire length of DNA involved with expression of a full-length mRNA. The sequences that are located 5' of the coding region, which sometimes are present on the mRNA, are referred to as upstream or 5' non-translated sequences (UTR). The untranslated (UTR) sequences which are located 3' or downstream of the coding region, which sometimes are present on the mRNA, are referred to as 3' non-translated sequences. The term "gene" encompasses both cDNA, genomic DNA and synthetic DNA. A genomic form or clone (copy) of a gene in a genome often contains the coding region interrupted with non-coding sequences termed "introns" or "intervening regions" or "intervening sequences." Introns are segments of a gene that may contain regulatory elements such as enhancers. Introns are removed or "spliced out" from a primary RNA transcript; introns therefore are absent in the messenger RNA (mRNA) transcript. The mRNA functions during translation to specify the sequence or order of amino acids in a nascent polypeptide.

In addition to containing introns, a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage and polyadenylation.

As used herein, the terms "heterologous" in reference to a nucleic acid sequence refers to a piece of DNA that is not in its natural environment (i.e., has been altered by the hand of man). For example, a heterologous nucleic acid sequence includes a piece of DNA from one species introduced into another species.

As used herein, the terms "heterologous gene" refers to a gene encoding a factor that is not in its natural environment (i.e., has been altered by the hand of man). For example, a heterologous gene includes a gene from one species introduced into another species. A heterologous gene also includes a gene that is synthetically reversed engineered from a protein (amino acid) sequence or a gene native to an organism that has been altered in some way (e.g., mutated, added in multiple copies, linked to a non-native promoter or enhancer sequence, etc.). Heterologous genes are distinguished from endogenous genes in that the heterologous gene sequences are typically joined to nucleotide sequences comprising regulatory elements such as promoters that are not found naturally associated with that gene for the protein encoded by the heterologous gene or with gene sequences in the chromosome, or are associated with portions of the chromosome not found in nature (e.g., genes expressed in loci where the gene is not normally expressed).

As used herein, the term "heterologous protein" refers to the protein expressed from a heterologous gene. Heterologous refers to the fact that often the transferred protein was initially cloned from or derived from a different cell type or a different species from the recipient. Typically the protein itself is not transferred, but instead the 'correctly edited' genetic material coding for the protein (the complementary DNA or cDNA) is added to the recipient cell. The genetic material that is transferred typically must be within a format that encourages the recipient cell to express the cDNA as a protein (i.e., it is put in an expression vector). Methods for transferring foreign genetic material into a recipient cell include transfection and transduction.

As used herein, the term "marker" as used herein refers to a protein and its encoding gene used for identifying expressed proteins or an enzyme having an activity that confers resistance to an antibiotic (ampicillin, kanamycin, chloramphenicol, zeocin, tetracycline, etc.) drug, or digestion of an indicator such as X-gal, upon the cell in which the marker for selection is expressed, or which confers expression of a trait which can be detected (e.g., luminescence or fluorescence). Examples are Flag, beta-galactosidase, green fluorescent protein (GFP), luciferase, xanthine phosphoribosyltransferase, antibiotic resistance, etc.

As used herein, the term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

As used herein, the term "host cell" refers to any cell capable of replicating and/or transcribing and/or translating a heterologous gene, such as a single cell or multiple cell organism.

As used herein, the term "algae" refers to a large, diverse group of photosynthetic eukaryotic organisms that are not necessarily closely related, and is thus polyphyletic. Included organisms range without limitation from unicellular microalgae, such as *Chlorella* and the diatoms, to multicellular forms, such as the giant kelp, a large brown alga which may grow up to 50 m in length. Most algae are aquatic and autotrophic and lack many of the distinct cell and tissue types, such as stomata, xylem, and phloem, which are found in land plants. The largest and most complex marine algae are called seaweeds, while the most complex freshwater forms are the Charophyta, a division of green algae which includes, for example, Spirogyra and stoneworts. Algae may be formed by one or more algal cells. And an algal cell as provided herein therefore refers to a cell forming an alga. In embodiments, an alga is a single algal cell. In embodiments, an alga is a plurality of algal cells.

As used herein, the term "green algae" refers to a diverse group of algae (singular: green alga), with more than 7000 species growing in a variety of comprising chlorophyll, which they use to capture light energy to fuel the manufacture of sugars, but unlike plants they are primarily aquatic. In other words, green algae are aquatic organisms that thrive on sunlight and carbon dioxide (or bicarbonate).

As used herein, the term "*Chlamydomonas*" in general refers to a single cell eukaryote organism within a genus of 500+ different species of unicellular photosynthetic green algae or "microplant" which often expresses two *flagella* for motility, along with a single chloroplast organelle which occupies the greater part of the cell. *Chlamydomonas* species are found in soil, fresh water, oceans, snow on mountaintops, etc., including the species *Chlamydomonas reinhardtii*. *Chlamydomonas* grow well heterotrophically (in darkness), and grows best when provided both light and organic acids (acetate), thus frequently found growing (viable) in polluted environments including environments containing insect larvae. *Chlamydomonas* are used for development of strains for use in bioremediation.

As used herein, the term "*Chlamydomonas reinhardtii*" refers to a species of *Chlamydomonas*. It is a single-cell green alga about 10 micrometers in diameter that swims with two *flagella*. It has a cell wall made of hydroxyproline-rich glycoproteins, a large cup-shaped chloroplast, a large pyrenoid, and an eyespot that senses light. *Chlamydomonas* species are widely distributed worldwide in soil and fresh water. *Chlamydomonas reinhardtii* is an especially well studied biological model organism, partly due to its ease of culturing and the ability to manipulate its genetics. When illuminated, *C. reinhardtii* can grow photoautotrophically, but it can also grow in the dark if supplied with organic carbon.

As used herein, the term "wild type" or "wild-type" in reference to *Chlamydomonas* organisms refers to organisms found in nature that were not modified or engineered. Wild type in reference to a strain refers to *Chlamydomonas* organisms that were isolated from nature and grown or maintained in a laboratory (an artificial environment).

As used herein, the term "strains" in reference to *Chlamydomonas* organisms refers to organisms within the same species or sub species having different functions or genetics, such that a transgenic *Chlamydomonas reinhardtii* expressing a heterologous protein, such as an enzyme from a different organism.

As used herein, the term "engineered" refers in general to an artificial process of manipulating nucleic acid sequences, such as by ligating (such as by using a ligase enzyme) two or more isolated nucleic acids sequences to each other, or synthesizing an artificial gene, or making a product, such as a transgenic *Chlamydomonas* organism.

As used herein, the term "compartments" or "organelles" in reference to a cell is used in its broadest sense. The term includes but is not limited to, the *flagella*, cilia, endoplasmic reticulum, Golgi apparatus, trans Golgi network, plastids including chloroplasts, proplastids, and leucoplasts, sarcoplasmic reticulum, glyoxysomes, mitochondrial, chloroplast, and nuclear membranes, and the like.

As used herein, the term "*flagella*" refers to a hair-like structure that acts primarily as an organelle of locomotion in the cells of many living organisms. Flagella, characteristic of the protozoan group *Mastigophora*, also occur on the gametes of algae, fungi, mosses, slime molds, and animals. Flagellar motion causes water currents necessary for respiration and circulation in sponges and coelenterates. Eukaryotes may have one to many *flagella*, which move in a characteristic whip-like manner. The *flagella* closely resemble the *cilium* in structure. The core is a bundle of nine pairs of microtubules surrounding two central pairs of microtubules (the so-called nine-plus-two arrangement); each microtubule is composed of the protein tubulin. The coordinated sliding of these microtubules confers movement. The base of the *flagellum* is anchored to the cell by a basal body. Most motile bacteria move by means of *flagella*. However, the structures and pattern of movement of prokaryotic and eukaryotic *flagella* are different.

As used herein, the term "*cilia*" refer to a short eyelash-like filament that is numerous on tissue cells of most animals and provides the means for locomotion of protozoans of the phylum *Ciliophora*. *Cilia* may be fused in short transverse rows to form membranelles or in tufts to form cirri. Capable of beating in unison, *cilia* move mammalian ova through oviducts, generate water currents to carry food and oxygen past the gills of clams, carry food through the digestive systems of snails, circulate cerebrospinal fluid of animals, and clean debris from the respiratory systems of mammals. In modified form, *cilia* trigger the discharge of stinging devices in jellyfish and give rise to the light-sensitive rods of the mammalian retina and the odour-detecting units of olfactory neurons. *Cilia* are composed of a central core (the axoneme), which contains two central microtubules that are surrounded by an outer ring of nine pairs of microtubules. The outer ring of microtubules is surrounded by a membrane that is continuous with the cell membrane; ciliary outgrowth is controlled by the basal body that is located just inside the cell surface at the base of the *cilium*. Beneath the surface of some cells, there is a network of fibrous rootlets or microtubular bundles that may provide support for the epithelium or coordinate ciliary beating.

As used herein, the term "axoneme" refers to the microtubule-based cytoskeletal structure that forms the core of a *cilium* or *flagellum*. Cilia and *flagella* are found on many cells, organisms, and microorganisms, to provide motility. The axoneme serves as the "skeleton" of these organelles, both giving support to the structure and, in some cases, the ability to bend. Though distinctions of function and length may be made between *cilia* and *flagella*, the internal structure of the axoneme is common to both. The axoneme of primary *cilia* typically has a ring of nine outer microtubule doublets (called a 9+0 axoneme), and the axoneme of a motile *cilium* has two central microtubules in addition to the nine outer doublets (called a 9+2 axoneme). The axonemal cytoskeleton acts as a scaffolding for various protein complexes and provides binding sites for molecular motor proteins such as kinesin II, that help carry proteins up and down the microtubules. In embodiments, the axoneme has the structure of FIG. 1A, 1B, or 1C. The term "axonemal protein" as provided herein refers to a protein forming the axoneme. In embodiments, the axonemal protein is FAP20, RSP3. IFT20, or DRC4. The term "axonemal function" refers to the function of a protein that is similar or the same as the function of an axonemal protein. A protein with axonemal function is a protein capable of carrying out the same function as an axonemal protein. In embodiments, the axonemal protein has the function of FAP20, RSP3, IFT20, or DRC4.

As used herein, the terms "intraflagellar transport" and "IFT" refer to a bidirectional motility along axonemal microtubules that is essential for the formation (ciliogenesis) and maintenance of most eukaryotic *cilia* and *flagella*. It is thought to be required to build all *cilia* that assemble within a membrane projection from the cell surface.

As used herein, the term "fusion protein" is used in accordance with its plain ordinary meaning and refers to a covalently-linked polypeptide chain derived from two or more different proteins or genes of origin. A fusion protein may include two or more proteins operably linked and expressed by one continuous nucleic acid sequence.

As used herein, the terms "FAP20" and "*flagella*-associated protein 20" are used in accordance with their plain and ordinary meanings and refer to any of the recombinant or naturally-occurring forms of a highly conserved flagellar-associated protein that is an inner junction (IJ) component or variants or homologs thereof that maintain FAP20 activity. In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring FAP20 polypeptide. In embodiments, the FAP20 is substantially identical to the protein identified by the UniProt reference number: A8IU92) or a variant or homolog having substantial identity thereto.

As used herein, the terms "IFT20" and "intraflagellar transport protein 20" are used in accordance with their plain and ordinary meanings and refer to any of the recombinant or naturally-occurring forms of a intraflagellar transport particle subunit or variants or homologs thereof that maintain IFT20 activity. In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IFT20 polypeptide. In embodiments, the IFT20 is substantially identical to the protein identified by the Uni-Prot reference number: Q81Y31) or a variant or homolog having substantial identity thereto.

As used herein, the terms "RSP3" and "radial spoke protein 3" are used in accordance with their plain and ordinary meanings and refer to any of the recombinant or naturally-occurring forms of radial spoke protein 3 or variants or homologs thereof that maintain RSP3 activity. Flagellar radial spokes contribute to the regulation of dynein arm activity and thus the pattern of flagellar bending. RSP3 is a highly conserved A-kinase anchoring protein located at the base of the radial spoke stalk and required for radial spoke assembly on the doublet microtubules. In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring RSP3 polypeptide. In embodiments, the RSP3 is substantially identical to the protein identified by the UniProt reference number: Q86UC2) or a variant or homolog having substantial identity thereto.

As used herein, the term "DRC4" is used in accordance with their plain and ordinary meanings and refer to any of the recombinant or naturally-occurring forms of DRC4 or variants or homologs thereof that maintain DRC4 activity. The nexin-dynein regulatory complex (N-DRC) is a key regulator of ciliary/flagellar motility, which maintains the alignment and integrity of the distal axoneme and regulates microtubule sliding in motile axonemes. In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring DRC4 polypeptide. In embodiments, the DRC4 is substantially identical to the protein identified by the UniProt reference number: 095995) or a variant or homolog having substantial identity thereto.

As used herein, the terms "expression vector" or "expression construct" are used in accordance with their plain and ordinary meanings and refer to any of the recombinant or naturally-occurring forms of a bacterial plasmid, bacmid, or virus or variants or homologs thereof that are for the use of expressing a target gene of interest as a protein product. The target of interest can be any gene of interest, including genes that encode for naturally-occurring proteins, any partial or modified variants of naturally-occurring proteins, chimeric proteins, tagged proteins, or de novo designed protein sequences. The expression vector must contain the elements necessary for gene expression, including, but not limited to, a promoter sequence, a ribosome-binding sequence, a start codon, the target of interest sequence, and a stop codon. The expression vector can be modified by any genetic engineering process or technique, including, but not limited to, polymerase chain reaction (PCR), restriction enzyme digest and DNA ligation, Gibson cloning, and CRISPR-related gene editing.

The terms "in operable combination", "in operable order" and "operably linked" as used herein refer to the linkage of nucleic acid sequences in such a manner that a nucleic acid sequence (such as a promoter) is capable of directing the transcription of a given gene and/or the synthesis of a desired protein.

The term "promoter" as used herein refers to a nucleotide sequence in DNA to which RNA polymerase binds to begin transcription. A promoter may be inducible or constitutive.

As used herein, the terms "control" or "control experiment" are used in accordance with its plain ordinary meaning and refer to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

As used herein, the term "expression" is used in accordance with its plain ordinary meaning and refers to any step involved in the production of a polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

As used herein, the term "biosensor", refers to a construct used for the detection of a chemical substance, that combines a biological component with a physicochemical detector. The sensitive biological element, e.g. tissue, microorganisms, organelles, cell receptors, enzymes, antibodies, nucleic acids, etc., is a biologically derived material or biomimetic component that interacts with, binds with, or recognizes the analyte under study. The biologically sensitive elements can also be created by biological engineering. The transducer or the detector element, which transforms one signal into another one, works in a physicochemical way: optical, piezoelectric, electrochemical, electrochemiluminescence etc., resulting from the interaction of the analyte with the biological element, to easily measure and quantify. The biosensor reader device connects with the associated electronics or signal processors that are primarily responsible for the display of the results in a user-friendly way. In embodiments, axonemes expressing a heterologous protein as described herein may form a biosensor.

As used herein, the term "substrate channeling" refers to the passing of the intermediary metabolic product of one enzyme directly to another enzyme or active site without its release into solution. When several consecutive enzymes of a metabolic pathway channel substrates between themselves, this is called a metabolon. Channeling can make a metabolic pathway more rapid and efficient than it would be if the enzymes were randomly distributed in the cytosol, or prevent the release of unstable intermediates. In embodiments, axonemes expressing one or more heterologous enzymes as described herein may be constructed for substrate channeling.

I. Compositions

In an aspect, provided herein is an axoneme-containing cell including a nucleic acid encoding a fusion protein. The fusion protein includes an axonemal protein linked to a heterologous protein, and the fusion protein provides axonemal function to the cell.

In embodiments, the axoneme-containing cell is a ciliated cell (cell that includes *cilia*). In embodiments, the *cilia* are motile *cilia*. In embodiments, the axoneme-containing cell including motile *cilia* is a protozoan cell. In embodiments, the protozoan cell is a *Ciliophora* cell. In embodiments, the axoneme-containing cell is a flagellar cell (a cell that includes a *flagellum* or *flagella*). In embodiments, the flagellar cell is, for example, a eukaryotic cell such as an algae cell.

In an aspect, provided herein is an algal cell including a nucleic acid encoding a fusion protein, where the fusion protein includes an axonemal protein linked to a heterologous protein through an enzyme cleavable linker, and where the fusion protein provides axonemal function to the algal cell.

In an aspect, provided herein is a plurality of algal cells where each algal cell includes a nucleic acid encoding a fusion protein, where the fusion protein includes an axonemal protein linked to a heterologous protein through an enzyme cleavable linker, and where the fusion protein provides axonemal function to the algal cell.

In embodiments, the algal cell is a *Chlamydomonas* cell. In embodiments, the algal cell is a *Chlamydomonas acidophil* cell, *Chlamydomonas caudata* cell, *Chlamydomonas ehrenbergii* cell, *Chlamydomonas elegans* cell, *Chlamydomonas moewusii* cell, *Chlamydomonas nivalis* cell, *Chlamydomonas ovoidae* cell, or a *Chlamydomonas reinhardtii* cell. In embodiments, the algal cell is a *Chlamydomonas acidophil* cell. In embodiments, the algal cell is a *Chlamydomonas caudata* cell. In embodiments, the algal cell is a *Chlamydomonas ehrenbergii* cell. In embodiments, the algal cell is a *Chlamydomonas elegans* cell. In embodiments, the algal cell is a *Chlamydomonas moewusii* cell. In embodiments, the algal cell is a *Chlamydomonas nivalis* cell. In embodiments, the algal cell is a *Chlamydomonas ovoidae* cell. In embodiments, the algal cell is a *Chlamydomonas reinhardtii* cell.

In embodiments, the nucleic acid provided herein is an expression vector. In embodiments, the expression vector provided herein includes coding sequence for the expression of a fusion protein, where the fusion protein includes an axonemal protein linked to a heterologous protein. In embodiments, the expression vector includes coding sequence for the expression of a fusion protein, where the fusion protein includes an axonemal protein linked to a heterologous protein through an enzyme cleavable linker.

In embodiments, the heterologous protein is selected from any pharmaceutically or industrially relevant protein. In embodiments, the heterologous protein is an antibody. In embodiments, the heterologous protein is a vaccine component. In embodiments, the heterologous protein is an enzyme.

In embodiments, the heterologous protein is an enzyme selected from oxidoreductase, transferase, hydrolase, lyase, isomerase, and ligase. In embodiments, the heterologous protein is an oxidoreductase enzyme selected from a dehydrogenase, oxidase, oxygenase, and peroxidase. In embodiments, the heterologous protein is a transferase enzyme selected from fructosyltransferase, transketolase, acytransferase, and transaminase. In embodiments, the heterologous protein is a hydrolase enzyme selected from a protease, amylase, acylase, lipase, phosphatase, and cutinase. In embodiments, the heterologous protein is a lyase enzyme selected from pectate lyase, hydratase, dehydratase, decarboxylase, fumerase, and argino succinase. In embodiments, the heterologous protein is an enzyme selected from isomerase, epimerase and racemase. In embodiments, the heterologous protein is an enzyme selected from ligase and synthetase.

In embodiments, the heterologous protein is an oxidoreductase. In embodiments, the heterologous protein is a dehydrogenase. In embodiments, the heterologous protein is an oxidase. In embodiments, the heterologous protein is an oxygenase. In embodiments, the heterologous protein is an peroxidase.

In embodiments, the heterologous protein is a transferase. In embodiments, the heterologous protein is a fructosyltransferase. In embodiments, the heterologous protein is a transketolase. In embodiments, the heterologous protein is acytransferase. In embodiments, the heterologous protein is a transaminase.

In embodiments, the heterologous protein is a hydrolase. In embodiments, the heterologous protein is a protease. In embodiments, the heterologous protein is an amylase. In embodiments, the heterologous protein is an acylase. In embodiments, the heterologous protein is a lipase. In embodiments, the heterologous protein is a phosphatase. In embodiments, the heterologous protein is a cutinase.

In embodiments, the heterologous protein is a lyase. In embodiments, the heterologous protein is a pectate lyase. In embodiments, the heterologous protein is a hydratase. In embodiments, the heterologous protein is a dehydratase. In embodiments, the heterologous protein is a decarboxylase. In embodiments, the heterologous protein is a fumerase. In embodiments, the heterologous protein is an argino succinase.

In embodiments, the heterologous protein is an isomerase. In embodiments, the heterologous protein is an epimerase. In embodiments, the heterologous protein is a racemase.

In embodiments, the heterologous protein is a ligase. In embodiments, the heterologous protein is a synthetase.

In embodiments, heterologous protein is an enzyme selected from acid proteinase, neutral proteinase, lipase, lactase such as β-galactosidase, aminopeptidase, catalase, transglutaminase, aylase, maltogenic α-amylase, xylanase, lipase, glucose oxidase, pectinase, cellulose, β-amylase, β-glucanase, Pullulanase, Naringinase, limoninase, phytase, xylanase, laccase, superoxide dismutase, endoglycosidase, glycosyl transferase, nitrile hydratase, glucose isomerase, acyltransferase, amidase, amyloglucosidase, manganese porxidase, lignin peroxidase, and oxygenase. In embodiments, heterologous protein is an acid proteinase. In embodiments, the heterologous protein is a neutral proteinase. In embodiments, the heterologous protein is a lipase. In embodiments, the heterologous protein is a lactase. In embodiments, the heterologous protein is a β-galactosidase. In embodiments, the heterologous protein is a aminopeptidase. In embodiments, the heterologous protein is a catalase. In embodiments, the heterologous protein is a transglutaminase. In embodiments, the heterologous protein is an aylase. In embodiments, the heterologous protein is a maltogenic α-amylase. In embodiments, the heterologous protein is a xylanase. In embodiments, the heterologous protein is a lipase. In embodiments, the heterologous protein is a glucose oxidase. In embodiments, the heterologous protein is a pectinase. In embodiments, the heterologous protein is a cellulose. In embodiments, the heterologous protein is a β-amylase. In embodiments, the heterologous protein is a β-glucanase. In embodiments, the heterologous protein is a Pullulanase, Naringinase. In embodiments, the heterologous protein is a limoninase. In embodiments, the heterologous protein is a phytase. In embodiments, the heterologous protein is a xylanase. In embodiments, the heterologous protein is a laccase. In embodiments, the heterologous protein is a superoxide dismutase. In embodiments, the heterologous protein is a endoglycosidase. In embodiments, the heterologous protein is a glycosyl transferase. In embodiments, the heterologous protein is a nitrile hydratase. In embodiments, the heterologous protein is a glucose isomerase. In embodiments, the heterologous protein is an acyltransferase. In embodiments, the heterologous protein is an amidase. In embodiments, the heterologous protein is an amyloglucosidase. In embodiments, the heterologous protein is a manganese porxidase. In embodiments, the heterologous protein is a lignin peroxidase.

In embodiments, the heterologous protein is an enzyme selected from retro-aldolase (K210M RA95.5-8)), Kemp-eliminase HG3.17 (KE), *Aspergillus niger* monoamine oxidase variant D5 (MAO), and NADH Oxidase (NOX), and beta-lactamase. In embodiments, heterologous protein is retro-aldolase (K210M RA95.5-8). In embodiments, heterologous protein is Kemp-eliminase HG3.17 (KE). In embodiments, heterologous protein is *Aspergillus niger* monoamine oxidase variant D5 (MAO). In embodiments, heterologous protein is NADH Oxidase (NOX). In embodiments, the heterologous protein is beta-lactamase.

In embodiments, the retro-aldolase (K210M RA95.5-8) is substantially identical to the protein identified by the NCBI accession number: 4PA8_A or a variant or homolog having substantial identity thereto. In embodiments, the Kemp-eliminase HG3.17 (KE) is substantially identical to the protein identified by the NCBI accession number: 5RG8_A or a variant or homolog having substantial identity thereto.

In embodiments, the *Aspergillus niger* monoamine oxidase variant D5 (MAO, MAO-N or also MAO-N-D5) is substantially identical to the protein identified by the PDB accession number: 2VVM_1 or a variant or homolog having substantial identity thereto. In embodiments, the NADH Oxidase (NOX) is substantially identical to the protein identified by the NCBI accession number: GAQ36973 or a variant or homolog having substantial identity thereto. In embodiments, the beta-lactamase is substantially identical to the protein identified by the NCBI accession number: GAQ36789 or a variant or homolog having substantial identity thereto.

In embodiments, the axonemal protein is selected from an intraflagellar transport protein, a radial spoke protein, a dynein arm protein, a nexin-dynein regulatory complex protein, and an axonemal microtubule-associated protein. In embodiments, the axonemal protein is an intraflagellar transport protein. In embodiments, the axonemal protein is a radial spoke protein. In embodiments, the axonemal protein is a dynein arm protein. In embodiments, the axonemal protein is a nexin-dynein regulatory complex protein. In embodiments, the axonemal protein is an axonemal microtubule-associated protein.

In embodiments, the axonemal protein is selected from FAP20, RSP3, IFT20, and DRC4. In embodiments, the axonemal protein is FAP20. In embodiments, the axonemal protein is RSP3. In embodiments, the axonemal protein is IFT20. In embodiments, the axonemal protein is DRC4.

In embodiments, the fusion protein provided herein includes an axonemal protein linked to a heterologous protein through an enzyme cleavable linker. In embodiments, the enzyme cleavable linker is a peptide linker. In embodiments, the enzyme cleavable linker is a β-glucuronidase linker. In embodiments, the enzyme cleavable linker is a protease cleavable linker. In embodiments, the enzyme cleavable linker is a Tobacco Etch Virus (TEV) protease cleavable linker.

In embodiments, the fusion protein provides axonemal function to the cell. In embodiments, providing axonemal function includes restoring flagellar or ciliary motility in a cell that has lost motility. In embodiments, providing axonemal function includes complementing an axonemal mutant cell that has lost axonemal function including flagellar or ciliary motility.

In an aspect, provided herein is a recombinant protein including an algal axonemal protein and a heterologous protein. The axonemal protein is linked to the heterologous protein through an enzyme cleavable linker and the recombinant protein provides axonemal function to the algal cell.

Embodiments of the recombinant proteins provided herein include any of the various algal axonemal proteins described herein. Embodiments of the recombinant proteins provided herein include any of the various heterologous proteins described herein. Embodiments of the recombinant proteins provided herein include algal axonemal proteins linked to a heterologous protein through any of the various enzyme cleavable linkers described herein.

In an aspect, provided herein is an isolated algal *flagella* that includes a flagellar membrane encompassing an axoneme, where the axoneme includes a fusion protein. The fusion protein includes an algal axonemal protein linked to a heterologous protein, and where the fusion protein provides axonemal function to the algal cell.

In embodiments, the isolated algal *flagella* provided herein include a *flagella* membrane encompassing an axoneme. In embodiments, the flagellar membrane is an outer membrane encompassing an axoneme.

Embodiments of the isolated algal *flagella* provided herein include an axoneme that includes a fusion protein of any of the various embodiments described herein. Embodiments of the isolated algal *flagella* encompassing an axoneme include fusion proteins that include any of the various algal axonemal proteins described herein. Embodiments of the isolated algal *flagella* encompassing an axoneme include fusion proteins that include any of the various heterologous proteins described herein. Embodiments of the isolated algal *flagella* encompassing an axoneme include algal axonemal proteins linked to a heterologous protein through any of the various enzyme cleavable linkers described herein.

In an aspect, provided herein is an isolated axoneme that includes a fusion protein, where the fusion protein includes an algal axonemal protein linked to a heterologous protein, and where the fusion protein provides axonemal function to the algal cell.

In an aspect, provided herein is a plurality of axonemes where each of the plurality of axonemes includes a fusion protein. The fusion protein includes an algal axonemal protein linked to a heterologous protein, and the fusion protein provides axonemal function to the algal cell.

Embodiments of the isolated axoneme or plurality of axonemes provided herein include a fusion protein of any of the various embodiments described herein. Embodiments of the axoneme or plurality of axonemes include fusion proteins that include any of the various algal axonemal proteins described herein. Embodiments of the axoneme or plurality of axonemes include fusion proteins that include any of the various heterologous proteins described herein. Embodiments of the axoneme or plurality of axonemes include algal axonemal proteins linked to a heterologous protein through any of the various enzyme cleavable linkers described herein.

In embodiments, the isolated plurality of axonemes provided herein are attached to a solid support. In embodiments, the solid support is selected from a glass slide, a multi-well plate, and the like. In embodiments, the solid support is a glass slide. In embodiments, the solid support is a multi-well plate.

In embodiments, the isolated axoneme or plurality of axonemes provided herein include one or more fusion proteins (e.g., 2, 3, 4, 5, 6, 7, 8, 8, 10, etc.), wherein each fusion protein includes any one of the axonemal proteins as described herein and any one of the heterologous proteins as described herein.

In embodiments, the isolated axoneme or plurality of axonemes provided herein compose (form) a biosensor and include a heterologous protein capable of binding a biomolecule, a cell, or a multicellular organism. In embodiments, the isolated axoneme or plurality of axonemes provided herein compose a biosensor and include a heterologous protein capable of binding to one or more of DNA, RNA, a vector, a virus vector, a peptide, a protein, an antibody, an antigen, a tissue factor, a lipid, a fatty acid, a steroid, a neurotransmitter, a vitamin, a toxin, a mineral, an inorganic ion, a free radical, a carbohydrate, a small molecule, an exons, a metabolite, a chromosome, a bacterium, a fungi, and/or a protozoa. In embodiments, the isolated axoneme or plurality of axonemes provided herein compose a biosensor and include a heterologous protein capable of binding to DNA. In embodiments, the isolated axoneme or plurality of axonemes provided herein compose a biosensor and include a heterologous protein capable of binding to RNA. In embodiments, the isolated axoneme or plurality of axonemes provided herein compose a biosensor and include a heterologous protein capable of binding to a vector. In embodiments, the isolated axoneme or plurality of axonemes provided herein compose a biosensor and include a heterologous protein capable of binding to a virus vector. In embodiments, the isolated axoneme or plurality of axonemes provided herein compose a biosensor and include a heterologous protein capable of binding to a peptide. In embodiments, the isolated axoneme or plurality of axonemes provided herein compose a biosensor and include a heterologous protein capable of binding to a protein. In embodiments, the isolated axoneme or plurality of axonemes provided herein compose a biosensor and include a heterologous protein capable of binding to an antibody. In embodiments, the isolated axoneme or plurality of axonemes provided herein compose a biosensor and include a heterologous protein capable of binding to an antigen. In embodiments, the isolated axoneme or plurality of axonemes provided herein compose a biosensor and include a heterologous protein capable of binding to a tissue factor. In embodiments, the isolated axoneme or plurality of axonemes provided herein compose a biosensor and include a heterologous protein capable of binding to a lipid. In embodiments, the isolated axoneme or plurality of axonemes provided herein compose a biosensor and include a heterologous protein capable of binding to fatty acid. In embodiments, the isolated axoneme or plurality of axonemes provided herein compose a biosensor and include a heterologous protein capable of binding to a steroid. In embodiments, the isolated axoneme or plurality of axonemes provided herein compose a biosensor and include a heterologous protein capable of binding to a neurotransmitter. In embodiments, the isolated axoneme or plurality of axonemes provided herein compose a biosensor and include a heterologous protein capable of binding to a vitamin. In embodiments, the isolated axoneme or plurality of axonemes provided herein compose a biosensor and include a heterologous protein capable of binding to a toxin. In embodiments, the isolated axoneme or plurality of axonemes provided herein compose a biosensor and include a heterologous protein capable of binding to a mineral. In embodiments, the isolated axoneme or plurality of axonemes provided herein compose a biosensor and include a heterologous protein capable of binding to an inorganic ion. In embodiments, the isolated axoneme or plurality of axonemes provided herein compose a biosensor and include a heterologous protein capable of binding to a free radical. In embodiments, the isolated axoneme or plurality of axonemes provided herein compose a biosensor and include a heterologous protein capable of binding to carbohydrate sensor. In embodiments, the isolated axoneme or plurality of axonemes provided herein compose a biosensor and include a heterologous protein capable of binding to small molecule. In embodiments, the isolated axoneme or plurality of axonemes provided herein compose a biosensor and include a heterologous protein capable of binding to an exon. In embodiments, the isolated axoneme or plurality of axonemes provided herein compose a biosensor and include a heterologous protein capable of binding to a metabolite. In embodiments, the isolated axoneme or plurality of axonemes provided herein compose a biosensor and include a heterologous protein capable of binding to a chromosome. In embodiments, the isolated axoneme or plurality of axonemes provided herein compose a biosensor and include a heterologous protein capable of binding to a bacterium. In embodiments, the isolated axoneme or plurality of axonemes provided herein compose a biosensor and include a heterologous protein capable of binding to a fungus. In embodiments, the isolated axoneme or plurality of axonemes provided herein compose a biosensor and include a heterologous protein capable of binding to a protozoa.

In embodiments, the isolated axoneme or plurality of axonemes provided herein form part of a biosensor, where the binding of the heterologous protein to a biomolecule, cell, or multicellular organism produces a detectable signal. In embodiments, the isolated axoneme or plurality of axonemes provided herein form part of a biosensor, where the binding of the heterologous protein to a biomolecule produces a detectable signal. In embodiments, the isolated axoneme or plurality of axonemes provided herein form part of a biosensor, where the binding of the heterologous protein to a cell produces a detectable signal. In embodiments, the isolated axoneme or plurality of axonemes provided herein form part of a biosensor, where the binding of the heterologous protein to a multicellular organism produces a detectable signal.

In embodiments, the detectable signal is selected from fluorescence, kinetic change of concentration, change of pH, change of visible color, and an electric potential change. In embodiments, the detectable signal is fluorescence. In embodiments, the detectable signal is kinetic change of concentration. In embodiments, the detectable signal is change of pH. In embodiments, the detectable signal is change of visible color. In embodiments, the detectable signal is an electric potential change.

In embodiments, the isolated axoneme or plurality of axonemes provided herein compose a construct suitable for substrate channeling. In embodiments, the isolated axoneme or plurality of axonemes provided herein include one or more fusion proteins, where each fusion protein includes any one of the axonemal proteins as described herein and any one of the heterologous proteins as described herein. The heterologous proteins may be enzymes involved in the production of a substrate. In embodiments, the arrangement of the enzymes on the isolated axonemes allow for substrate channeling.

II. Methods of Use

In an aspect, provided herein is a method of isolating a heterologous protein including expressing a fusion protein in an axoneme of a cell where the fusion protein includes an axonemal protein linked to a heterologous protein through a cleavable linker; separating the fusion protein from the *flagella*; and contacting the fusion protein with an enzyme thereby isolating said heterologous protein. For the methods provided herein any of the compositions provided including embodiments are contemplated.

In an aspect, provided herein is a method of isolating a heterologous protein including expressing a fusion protein in an algal *flagella* of an algal cell where the fusion protein includes an algal axonemal protein linked to a heterologous protein through a cleavable linker; separating the fusion protein from the algal *flagella*; and contacting the fusion protein with an enzyme thereby isolating said heterologous protein.

In embodiments, the method of isolating a heterologous protein provided herein includes expressing a fusion protein according to any of the various embodiments described herein. In embodiments of the methods provided herein, the fusion protein includes an axonemal protein linked to a heterologous protein through a cleavable linker.

In embodiments, separating includes detaching *flagella* expressing fusion protein from cells thereby forming detached *flagella*. In embodiments, separating includes detaching algal *flagella* expressing fusion protein from algal cells thereby forming detached *flagella*. In embodiments, detaching *flagella* includes exposing cells to pH shock and centrifugation to produce purified *flagella*. In embodiments, detaching algal *flagella* includes exposing algal cells to pH shock and centrifugation to produce purified algal *flagella*. In embodiments of the methods provided herein, the detached *flagella* includes a fusion protein that includes an axonemal protein linked to a heterologous protein through a cleavable linker.

In embodiments, the axonemal protein includes any of the various embodiments provided herein. In embodiments, the algal axonemal protein is selected from FAP20, RSP3, IFT20, and DRC4. In embodiments, the axonemal protein is FAP20. In embodiments, the axonemal protein is RSP3. In embodiments, the axonemal protein is IFT20. In embodiments, the axonemal protein is DRC4.

In embodiments, the heterologous protein includes any of the various embodiments provided herein. In embodiments, the heterologous protein is an enzyme as described according to the various embodiments provided herein.

In embodiments, separating further includes isolating an axoneme from a detached *flagella*. In embodiments of the methods provided herein, the isolated axoneme includes a fusion protein that includes an axonemal protein linked to a heterologous protein through a cleavable linker.

In embodiments, contacting the fusion protein with an enzyme thereby isolating said heterologous protein where the enzyme cleaves the fusion protein at the cleavable linker. In embodiments, the enzyme that cleaves the fusion protein at the cleavable linker is a protease. In embodiments, the enzyme that cleaves the fusion protein at the cleavable linker is Tobacco Etch Virus (TEV) protease.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1: Experimental Design for Cell-Based Biosynthesis of Linear Protein Arrays Described herein is an approach for using the *flagella* axoneme as the basis for biological self-assembling protein nanoarrays. The axoneme is the insoluble protein core of the eukaryotic *flagellum* or *cilium*. By attaching a protein of interest to particular axonemal proteins, it is possible to exploit the intraflagellar transport (IFT) system to incorporate those proteins into the axoneme as it assembles. Using the axoneme as a protein array confers several advantages, such as high protein loading capacity compared to other bioparticle systems, genetically programmed self-assembly without the need for any linking steps, single-step purification of particles without the need for cell lysis, allowing retention and re-use of biomass, and choice of isolating the particle as a membrane enclosed vesicle or as an exposed protein array. Several potential axonemal proteins were tested as adaptor proteins, using green fluorescent protein (GFP) as a test case. Data showed that FAP20 was an ideal scaffold protein for this purpose in that it shows high incorporation and uniform localization. Data showed that FAP20-GFP constructs were stably associated with the axoneme during purification and storage and that the GFP moiety can be released by protease cleavage.

Figure 1B:
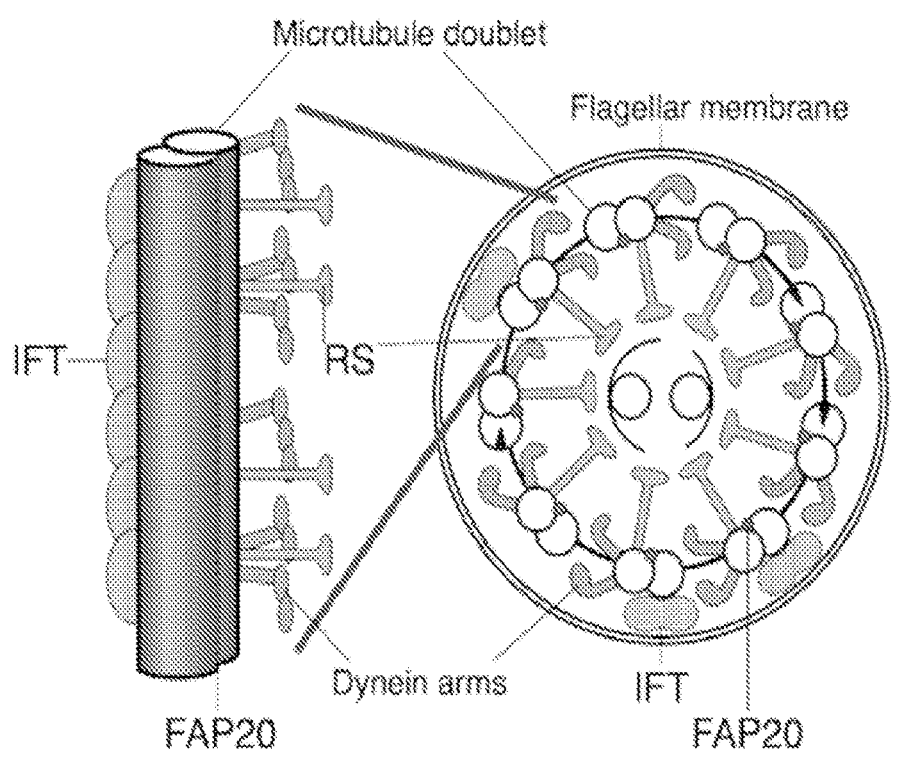
Figure 1C:
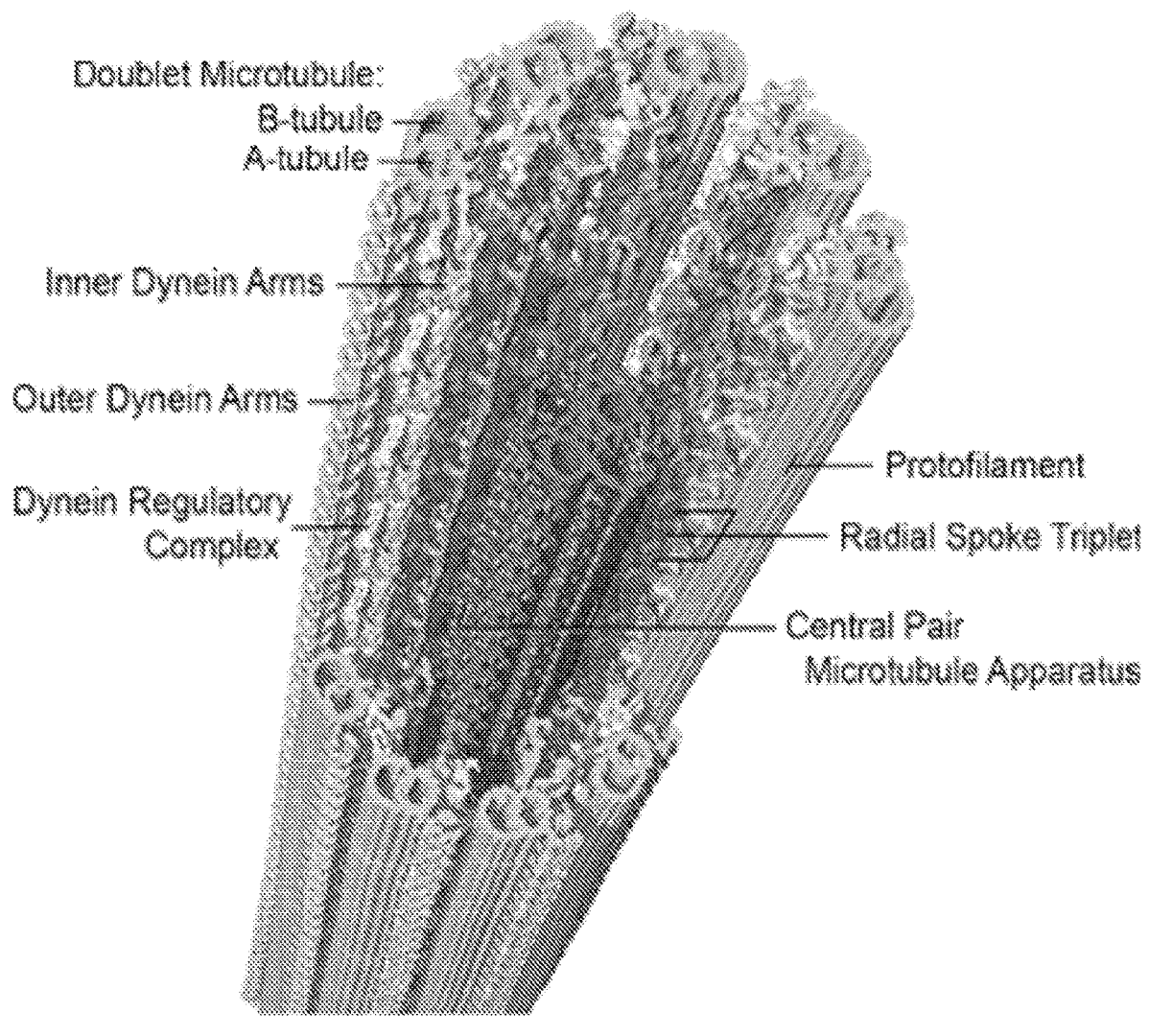
Figure 2A:
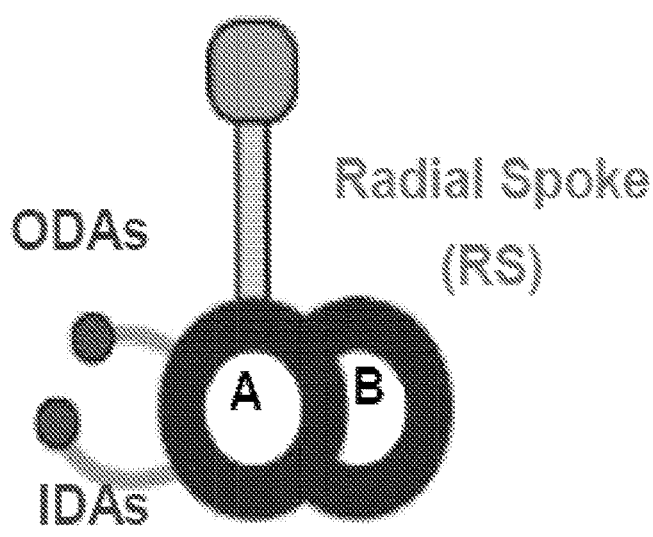
FIGS. 2A-2B present model representations of doublet microtubules (DMTs) tagged with fusion proteins.
Figure 2B:
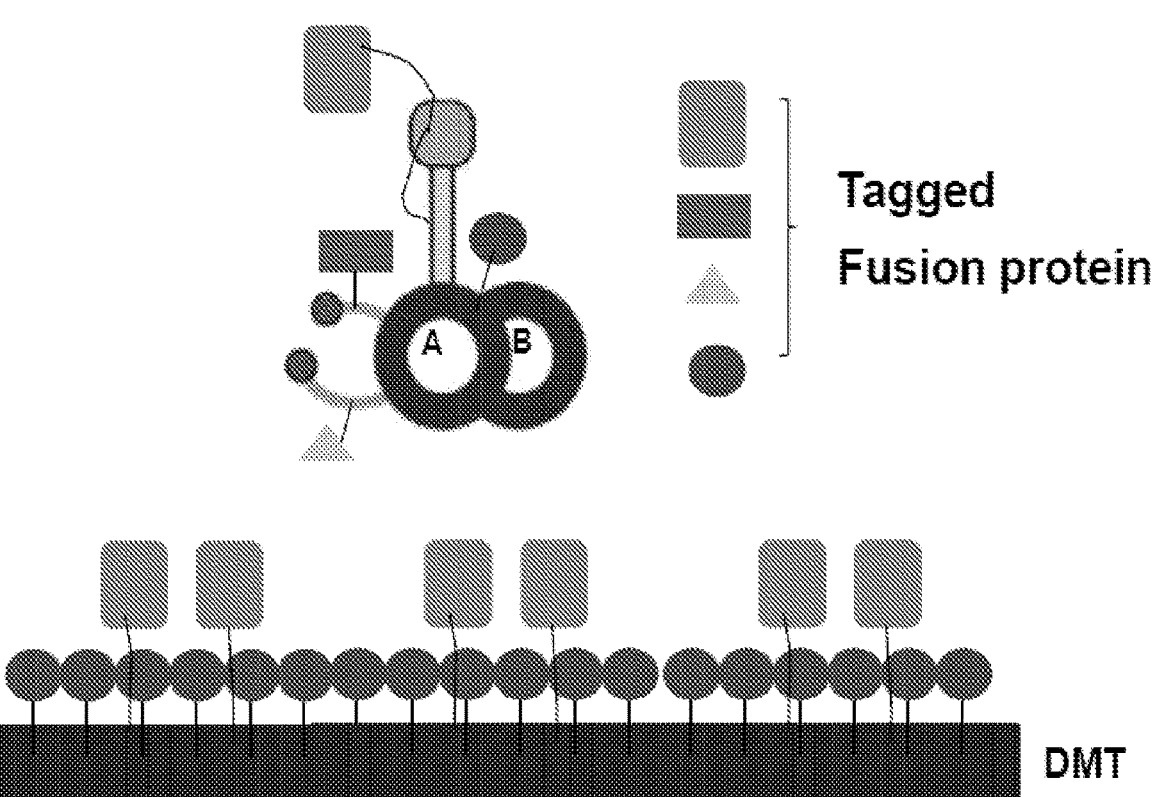

The axoneme of *cilia* and *flagella* (FIG. 1A) presented an alternative platform for constructing linear protein nanoarrays. The eukaryotic *flagellum* or *cilium* (the two terms are interchangeable) is a motile structure that consists of a protrusion of the plasma membrane supported by the axoneme, a protein-based assembly consisting of nine doublet microtubules together with several hundred associated proteins involved in building the axoneme and driving flagellar motility (FIG. 1C). In contrast to nanoparticles or ruler-based linear systems, axonemes typically are several orders of magnitude larger, on the 1-10 micron length scale. But unlike other large linear arrays such as microtubules or actin filaments, axonemes are subject to narrow length variation, typically showing a sharper-than-Gaussian length distribution (see for example, Ref. 12). The exact mechanism by which this length control takes place remains unclear, although a number of models have been proposed (see for example, Ref. 13). Importantly, the length of the axoneme can be tuned using a collection of existing mutations, including mutants that have *flagella* that are longer than normal, and other mutants that have shorter *flagella* (see for example, Refs. 14-18). Length can also be tuned using chemical inhibitors, for example, lithium causes *flagella* to increase length, while other compounds obtained in chemical screens cause *flagella* to shorten (see for example, Refs. 19-21). Flagellar length is thus tunable via both genetic and chemical means.

A complex molecular machinery known as the intraflagellar transport (IFT) system (FIG. 1B) uses a combination of motors and protein chaperones to transport insoluble proteins into the axoneme and incorporate them into the appropriate positions. Many different proteins incorporate into the axoneme with fixed spatial repeats, for example, radial spokes and dynein arms binds to the axoneme with an underlying 96 nm periodicity that is generated by molecular rulers aligned to the axonemal lattice (see for example, Ref. 12). The availability of multiple distinct docking sites with precisely equal periodicities raises the potential to combine multiple proteins into mixed arrays of highly defined local architectures. For example, one can imagine that two or more enzymes in a pathway could be coupled to axonemes in different but alternating spatial patterns allowing them to readily channel products from one enzyme to the next. (See for example, Refs. 22-25)

Compared to other types of biological nano-particles, axonemes are extremely easy to purify. As diagrammed in FIG. 5A and FIG. 6, *flagella* can be detached from living cells and purified with a single centrifugation step because the cell body is much larger than the *flagellum*. The axoneme can then be obtained by treating the purified *flagella* with detergent. For isolated axonemes, protein domains anchored to the axonemal array can be released by protease cleavage, allowing the axoneme to serve as a protein expression system, alternatively they may remain attached to the axoneme, providing immobilization of enzymes in a stable form without the need for any specific immobilization process.

As a source of biological material, experiments described herein utilized the unicellular green alga *Chlamydomonas reinhardtii*, a genetically tractable green alga that is easy to grow in large cultures using inexpensive media, and has been considered as a potential organism for production of algal biofuel (See for example, Refs. 14 and 26). Each *Chlamydomonas* cell has two *flagella*, and these can be easily separated from the cell body as discussed below. If a means existed for anchoring a protein of interest onto the axoneme of *Chlamydomonas*, this would potentially create a way to build self-assembling linear protein arrays with large protein capacity, tunable length, defined periodicity of binding, and easy storage, that could be produced in large quantities at low cost.

A key challenge in harnessing the axoneme as protein nanoarray was finding a way to incorporate a protein of interest into the axonemal structure. In order for a protein to incorporate into the axoneme, it must first be imported into the *flagellum*, then transported to the appropriate site on the axoneme, and ultimately must bind appropriately. Each of these steps of flagellar import, transport, and binding, are mediated by different proteins and recognition motifs, and in most cases the field is only beginning to understand these molecular interactions (see for example, Refs. 27-29). Thus, engineering a protein of interest, such as an enzyme or antigen, to become an axonemal protein would be a non-trivial task. An alternative approach was proposed, which was to use an existing axonemal protein as an adaptor (FIG. 1B). By expressing a fusion protein construct of a protein of interest with the axonemal protein, it could then be incorporated into the axoneme and would then benefit from all the advantages of the naturally occurring axonemal protein (high quantity, reproducible length of array, uniform spatial distribution, and stability during storage). The challenge is that many axonemal proteins exist as part of larger complexes. A fusion construct would only work if it did not disrupt the protein interactions involved in forming the complex during axonemal assembly. The axoneme is a highly complex structure containing hundreds of different proteins. In principle, any of these could be used as an adaptor by fusing a protein domain of interest, such as an enzyme, onto one end of the axonemal protein. The ideal adaptor protein would retain its function when other proteins are fused onto it, in order to allow transformants with his levels of expression to be quickly identified. The strategy is to express the adaptor fusion construct in mutant cells that lack the endogenous copy of the adaptor protein-encoding gene. Because axonemal proteins are required for proper swimming motility, the adaptor-less mutants are non-motile. When the fusion construct is expressed, the missing axonemal protein is restored and swimming motility is regained. Simple assays were used to identify swimming cells from large numbers of non-motile strains, leading to rapid isolation of high-expressing strains. Implementation of this strategy required that the adaptor protein continues to function when fused to a protein of interest. Other ideal features would be highly uniform distribution along the axoneme, high density of incorporation, stable attachment even during freezing and thawing, and biochemical accessibility within the final assembled structure.

Experiments described herein investigated several axonemal protein complexes to determine suitability as an axonemal anchoring protein. In embodiments, the inner junction complex protein FAP20 showed the most abundant incorporation, reproducible total quantity, and the most spatially uniform distribution within the linear array. Analysis of isolated axonemes confirmed that FAP20 fusion proteins were stably maintained during axonemal isolation and storage. It was demonstrated that protein domains attached to FAP20 with a TEV protease cleavable linker can be released by protease treatment. This study represents a fundamental step towards development of the axoneme as a biologically self-assembled protein nanoarray.

Example 2: Experimental Results for Cell-Based Biosynthesis of Linear Protein Arrays Evaluating Potential Adaptor Proteins Based on Quantity of Incorporation.

In order to select one of these proteins as an adaptor onto which a guest protein of interest could be docked, three proteins that were already known to satisfy the key requirement of tolerating fusion with a guest protein while retaining their function were tested. As a second a priori requirement, proteins for which loss of function mutations already exist in *Chlamydomonas* were required. This second requirement was necessary because not all *Chlamydomonas* cells transformed with a transgene will express the gene, and so by transforming a mutant cell with a transgene expressing a fusion with a functional copy of the axonemal protein, one can identify transformants expressing the transgene based on rescue of the mutant phenotype. Three candidate adaptor proteins were examined: IFT20, RSP3, and FAP20. IFT20 is part of a kinesin motor complex that moves cargo proteins back and forth within the *flagellum* as part of the intraflagellar transport system. RSP3 is part of the radial spoke complex, a protein array located on the inner edge of the outer doublet microtubules, that regulates the flagellar beating cycle. RSP3 is encoded by the PF14 gene, and pf14 loss of function mutants have paralyzed *flagella*. FAP20 is a component of the inner junctional complex, a protein complex located at the juncture between the A and B tubules of the outer doublet. The relative locations of these three adaptor proteins are shown in FIG. 1B. (See for example, Refs. 31-33).

Figure 3A:
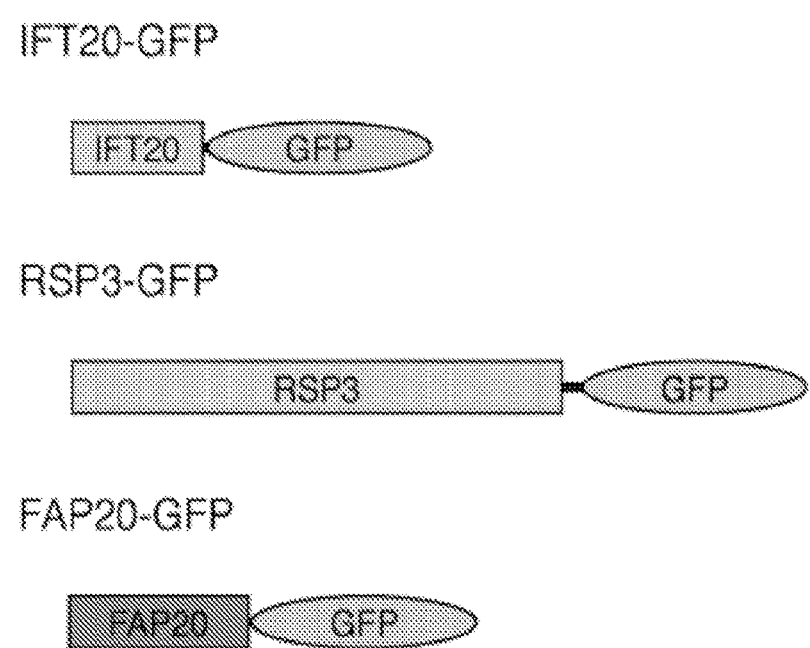
FIGS. 3A-3B present adaptor proteins for axonemal nanoarray.
Figure 3B:
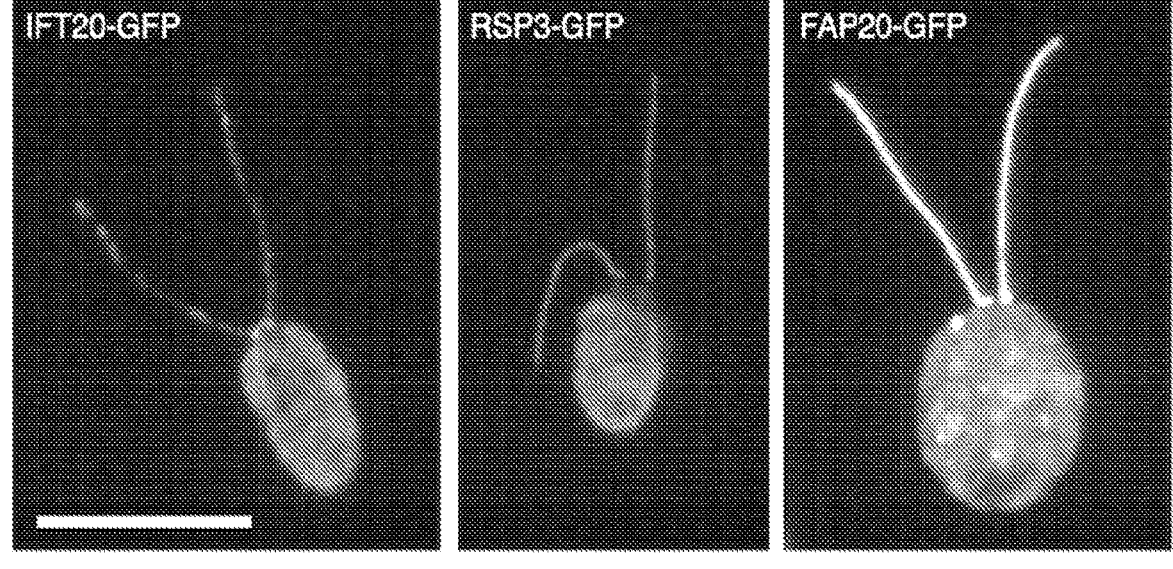

To evaluate these three adaptors, cells expressing GFP-tagged versions of the candidate adaptor proteins were examined. Fusions of IFT20, RSP3, and FAP20 (FIG. 3A) have all been previously described in the literature. Importantly, all three were shown to rescue loss of function mutations in the corresponding gene even when fused to GFP, indicating that the GFP fusion does not interfere with function. Visual comparison (FIG. 3B) showed that FAP20GFP showed the brightest signal, indicating the largest quantity of protein incorporated into the axoneme, while IFT20 showed the weakest signal.

Figure 4A:
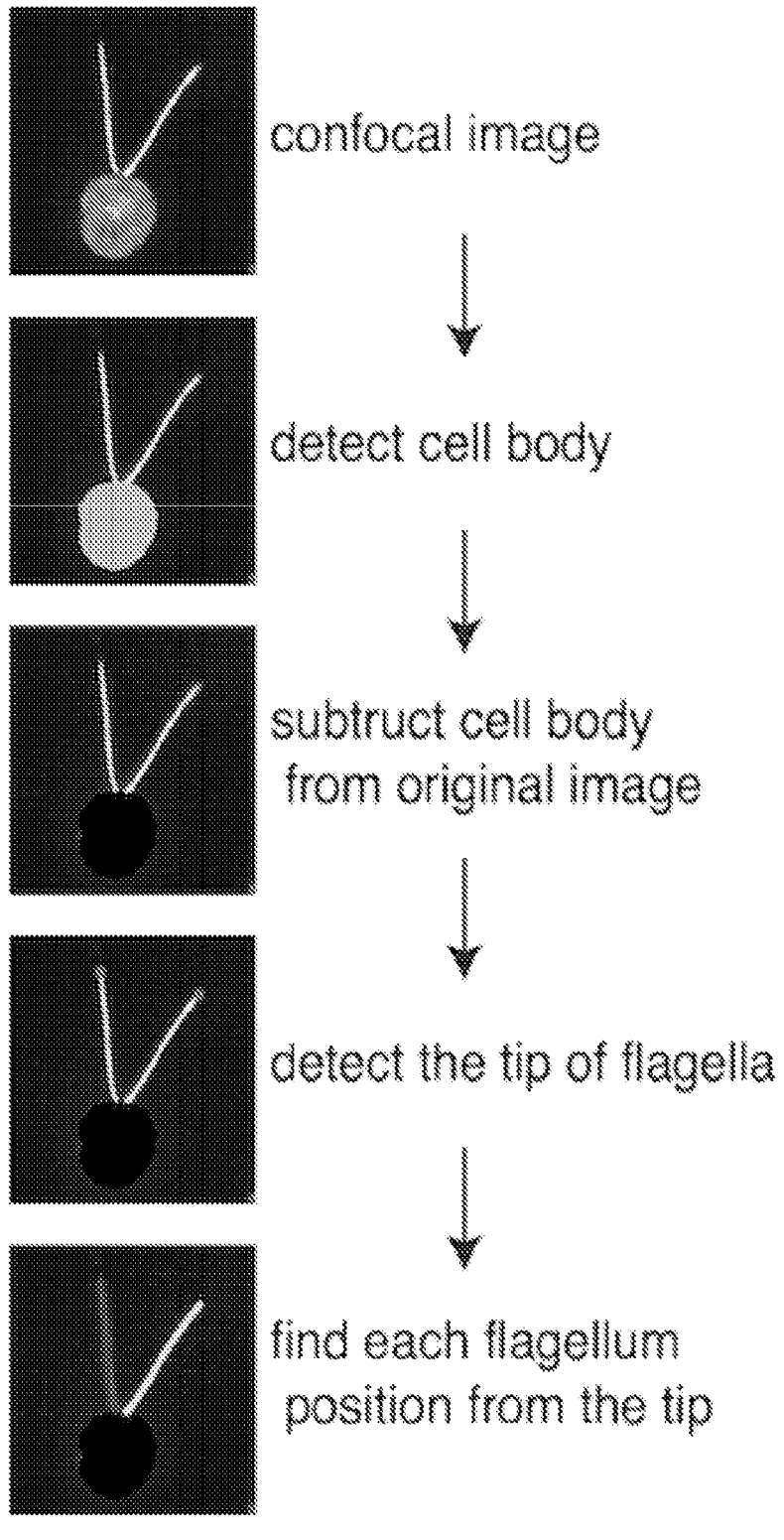
FIGS. 4A-4C present data related to the quantification of GFP incorporation into *flagella*.
Figure 4B:
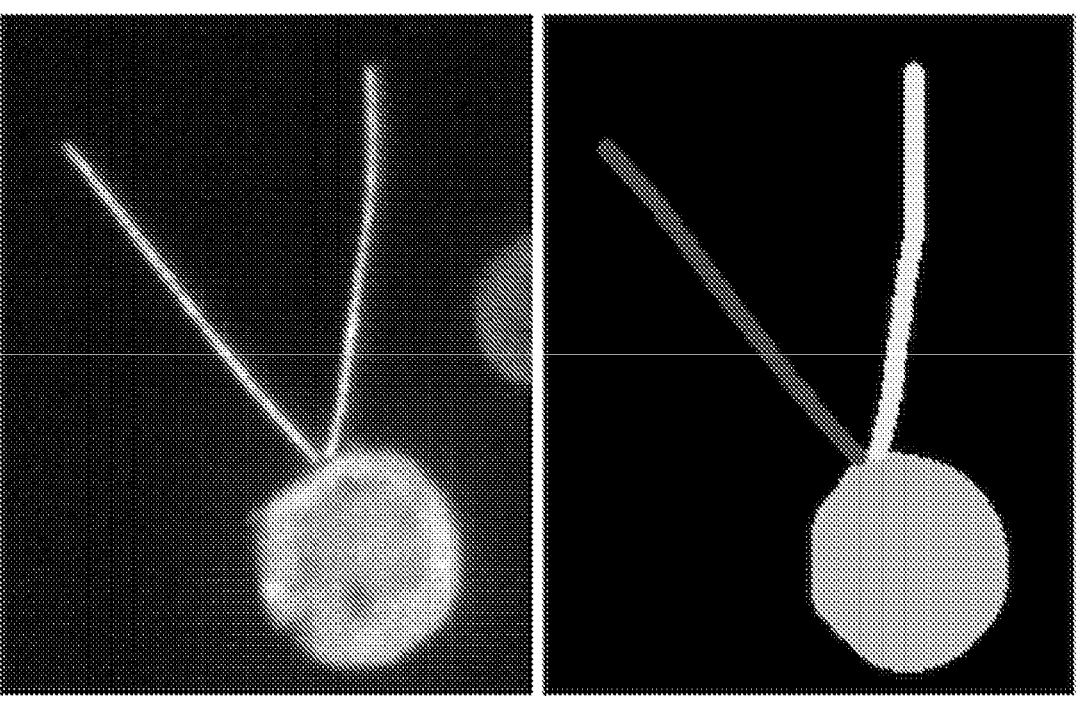
Figure 4C:
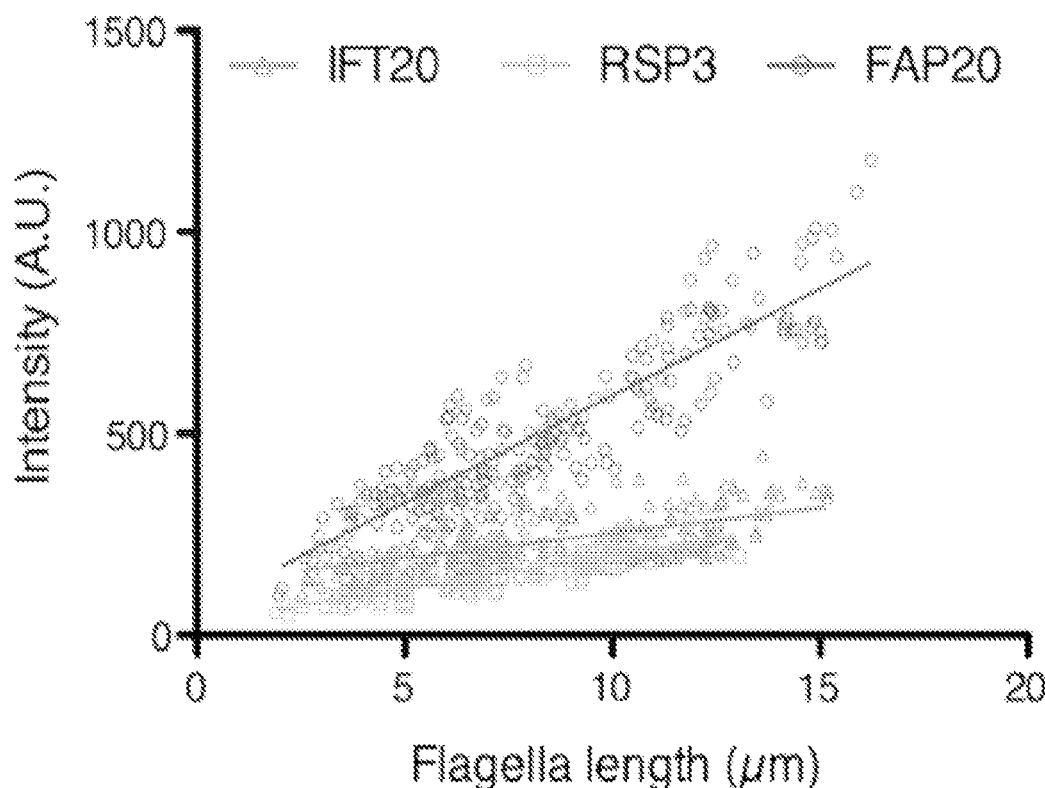

In order to quantify the incorporation, an automated procedure was developed to segment *flagella*, trace the linear background of each *flagellum*, and quantify the fluorescence intensity as a function of position (FIG. 4A). Segmentation of *flagella* was implemented by first segmenting the cell body, then removing it from the image, and then traversing the axes of the two *flagella* starting at the tips. This segmentation approach was able to reliably label each *flagellum* separately from the cell body (FIG. 4B) allowing GFP levels to be quantified. Using this algorithm, the total fluorescence intensity in each of the three strains was quantified (FIG. 4C). For all three constructs, the total intensity scaled linearly with flagellar length. This analysis showed that for all flagellar lengths examined, in embodiments, FAP20GFP gave the highest total intensity, and RSP3 the lowest, suggesting that in embodiments, FAP20 scaffold is more effective than the other two in total incorporation of GFP guest protein. For example, scatter of points around the best fit lines in FIG. 3C indicated that IFT20 shows substantially greater variation than RSP3 which had a similar average intensity. This was not surprising given that the IFT complex actively moves not only along the *flagellum* but also in and out of the flagellar compartment.

The primary conclusions from this analysis were that incorporation is directly proportional to length, indicating a constant level of incorporation per unit length, and that compared to IFT20 and RSP3, FAP20 showed a higher level of incorporation per unit length. Also noted in FIG. 3 was that FAP20 showed the most spatially uniform incorporation along the length of the *flagellum*. We concluded that FAP20 is the superior adaptor protein among the three that were tested here.

Stability During Axonemal Isolation and Storage

Figure 5A:
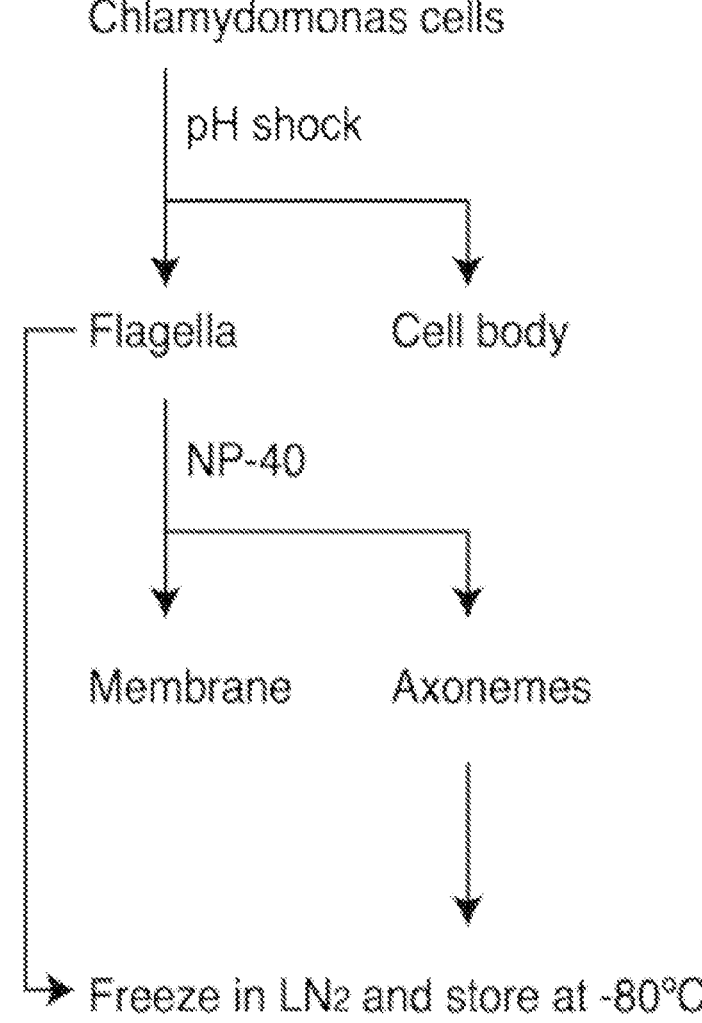
FIGS. 5A-5B present a diagram and microscopy images related to the stability of FAP20-GFP during nanoarray isolation and storage.

In order for any sort of nanoparticle or nanoarray to be useful in practice, it must be easily isolated and highly stable during both isolation and storage. First, the ability to isolate the nanoarrays away from the rest of the cell was tested. *Chlamydomonas* cells have a robust stress response called flagellar autotomy, in which the cell severs *flagella* at the base when placed under stress conditions, for example pH shock (see for example, Ref. 34). During flagellar autotomy, the *flagella* are pinched off at the base, leaving an intact *flagellum* including its bounding membrane. The *flagella* can then be cleanly separated away from the cell bodies by centrifugation through a sucrose cushion. These *flagella* can then be frozen down for storage or else de-membranated to produce isolated axonemes. Demembranation may be critical for many applications, for example if enzymes are coupled to the scaffold, since removal of the membrane will allow access of enzymes to the substrate in the surrounding media. For many applications, it may be important to be able to store the protein arrays, which was accomplished by freezing in liquid nitrogen and storage at −80 C. The complete workflow, including flagellar isolation, cell body recovery, de-membranation to produce axonemes, and storage at −80 C, is illustrated in FIG. 5A.

Figure 5B:
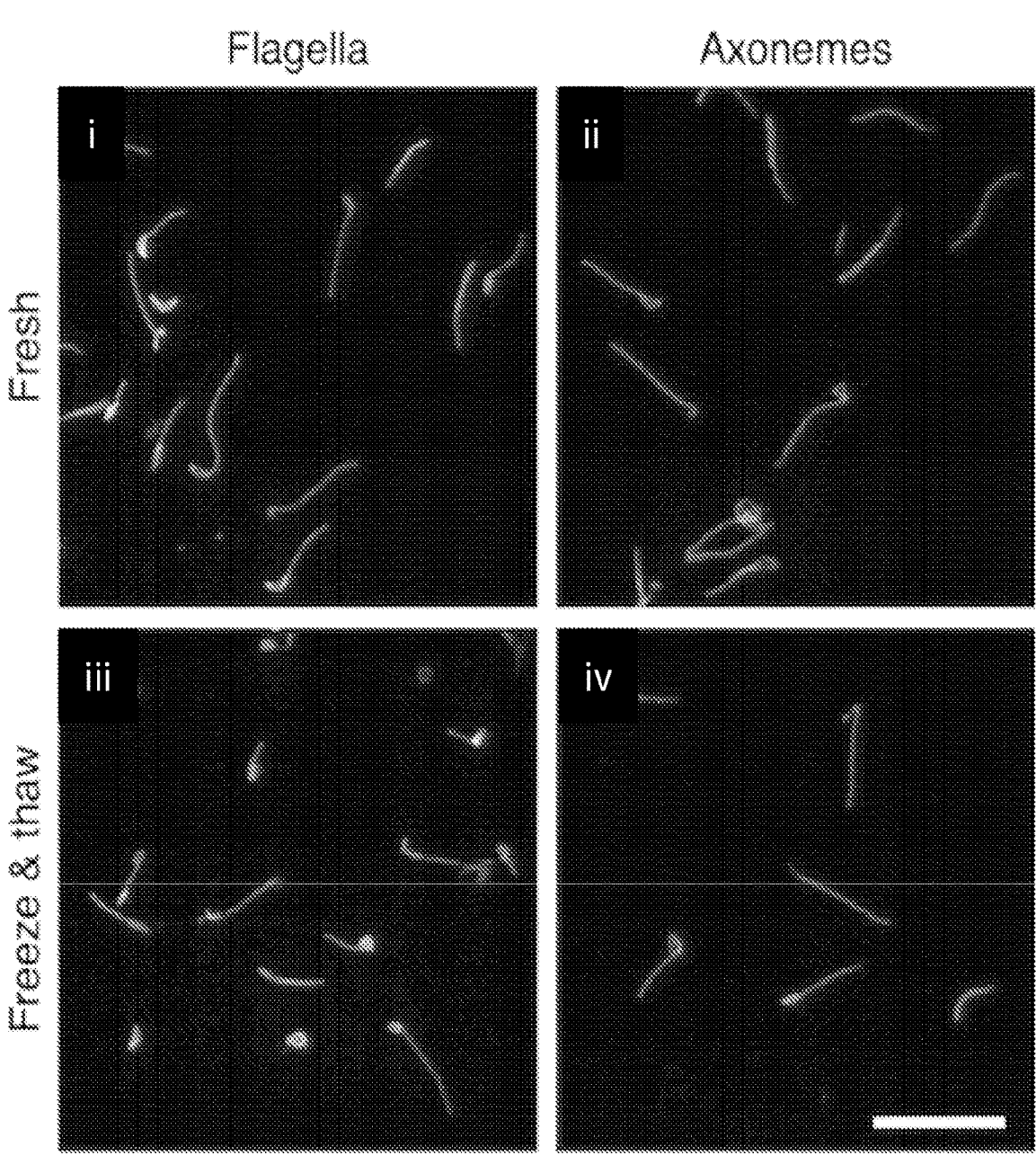

Axonemes are known to be stable structures overall, but the stability of individual axonemal proteins has not been systematically addressed. To test the stability of incorporation of FAP20-GFP, first *flagella* were isolated from expressing cells, and found to continue to show strong and uniform fluorescence (FIG. 5B, panel B). GFP fluorescence continued to be visible following de-membranation to produce axonemes (FIG. 5B, panel C), confirming the stability of attachment of FAP20 to the axoneme even when fused to another protein. For both *flagella* and axonemes, GFP fluorescence continued to be visible after freezing and thawing (FIG. 5B, panels D and E).

Release of Attached Proteins by TEV Protease Cleavage

Figure 7A:
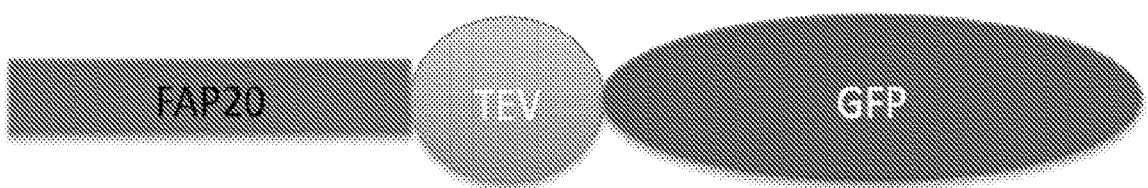
FIGS. 7A-7B present data related to the release of fusion constructs by TEV protease treatment.
Figure 7B:
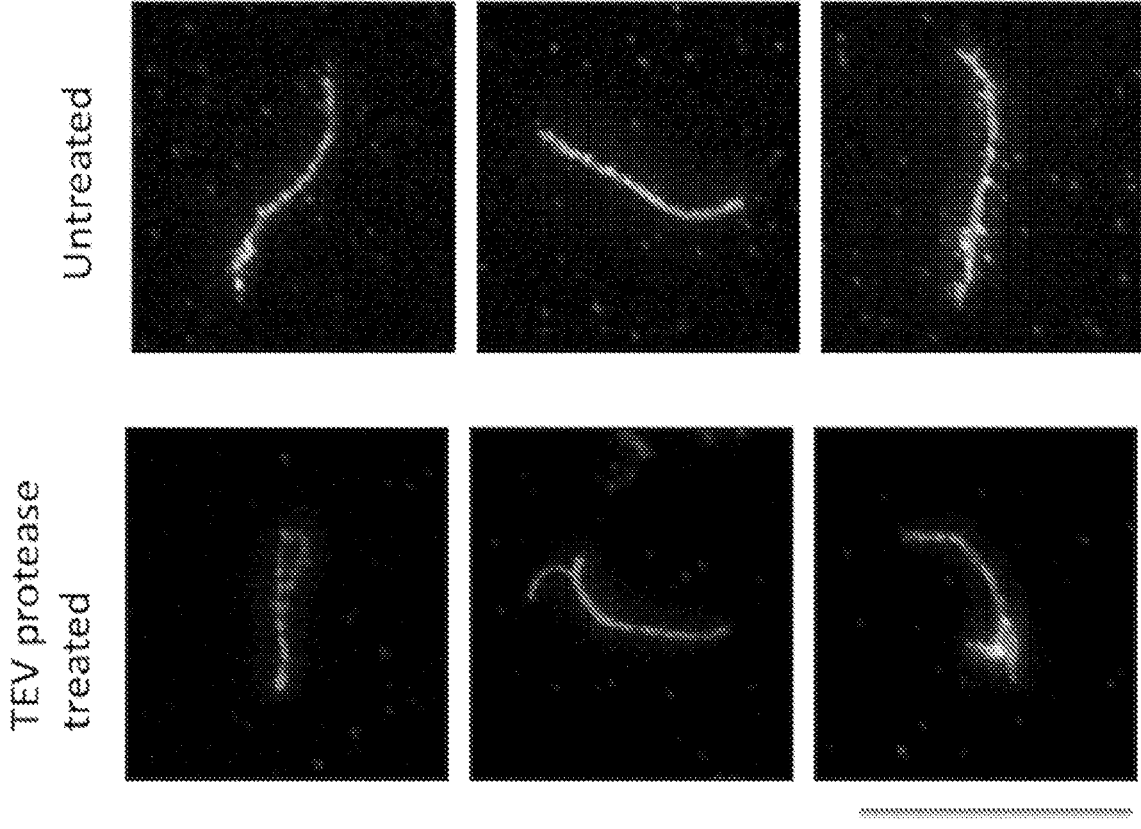

The axoneme attachment system has been described primarily as a way to generate self-assembling protein nanoarrays. However, given the ability to purify *flagella* cleanly in a single step, combined with the ability of the flagellar assembly system to handle insoluble proteins, it is proposed that axonemal protein arrays might also be useful as protein expression systems. In this case, a method would be needed to release the protein from the rest of the axoneme. To test this idea, a variant construct in which the FAP20 and GFP domains were linked by a linker containing a TEV protease cleavage site was generated (FIG. 7A). Flagella were harvested from strains expressing this construct, and used to prepare axonemes. In order to be able to detect axonemes from which GFP would have been removed, it was necessary to perform immunofluorescence with an antibody specific for acetylated tubulin, a protein highly enriched in axonemes. Double labeling with antibodies against GFP showed that the vast majority of GFP was removed following TEV protease treatment of the isolated axonemes (FIG. 7B). This result confirms that the axoneme can be used as a protein expression platform from which associated proteins can be released by protease cleavage.

Example 3: Discussion

The work described herein showed that FAP20 can be used as a scaffold protein to link domains of interest into linear protein arrays with high incorporation efficiency, spatial uniformity, simple isolation, and stability during storage. Applications of this system are comparable to those of other self-assembling nanoparticles, the primary difference being the vastly increased quantity of protein that can be packaged into a single axoneme. Without being bound to any specific theory, the packing density may not be higher, but the total quantity contained in one particle may be orders of magnitude larger due to the larger size of the axonemal array. Depending on the substrate availability through the flagellar membrane, the intact isolated *flagellum* might be able to be used as a self-contained bioreactor in which specific enzymes can be assembled using FAP20. The *flagella*/axoneme protein array is much easier and cheaper to purify compared to other nanoparticle systems, and does not require any in vitro processing steps to link enzymes into the scaffold.

Variability in axonemal nanoarray protein incorporation may be the result of two underlying sources of variation: variation in incorporation per unit length between cells and variation in the flagellar length. Because of the high uniformity of FAP20-GFP incorporation, both spatially within a *flagellum* and across a population of cells, the primary remaining contribution to variation in total quantity was the variation in flagellar length. It is known that flagellar length varies slightly during the cell cycle, hence variation can be reduced by arresting the cell cycle, for example by using nitrogen starvation to produce gametes. Mutants have been found to alter the flagellar length distribution, potentially providing an alternative approach to modulating length variation (see, for example, Ref. 12). Recently, it has been found that the flagellar length distribution becomes constricted at a specific time point during flagellar regeneration, allowing a 50% reduction in the standard deviation of the length distribution to be achieved simply by transiently lowering the pH of the media and then harvesting *flagella* three hours later (see, for example, Ref. 35). Further evaluation of methods to reduce and control flagellar length variation will be critical for development of the axonemal nanoarray as a useful expression system.

Example 4: Materials and Methods for Cell-Based Biosynthesis of Linear Protein Arrays

*Chlamydomonas* Culture and Imaging

*Chlamydomonas* cultures were grown following standard procedures. *Chlamydomonas* cells during regeneration of *flagella* were attached on polylysine-coated coverslips and fixed with 4% paraformaldehyde/PBS for 5 minutes. Fixed cells were mounted in VECTASHIELD® medium (Vector Laboratories, Burlingame, CA) on a slide glass and observed on an inverted microscope (Eclipse Ti; Nikon, Japan) with a 100× oil objective (Apo TIRF, NA 1.49; Nikon), spinning disk confocal system (CSU-22; Yokogawa Electric Corporation, Japan) and an EMCCD camera (Evolve Delta; Photometrics, Tucson, AZ). Z-stack images were taken at 0.2-μm interval.

The length and fluorescent intensity of *flagella* were measured using routines in MATLAB® (Math Works, Natick, MA). Z-stack images were convolved with a three-dimensional Gaussian filter to detect the cell body position. The cell body was subtracted the original z-stack images and then the position of flagellar tips was detected. Flagellar position was identified from the flagellar tip step by step on the basis of the intensity.

Preparation and Storage of *Flagella* and Axonemes

Isolation of *flagella* were performed as described Ref. 30. In short, the FAP20-GFP or FAP20-TEV-GFP strain was cultured in the TAP medium at 25° C. with constant aeration in light. Flagella were released from the cell body using the pH shock method. Isolated *flagella* were treated with 1% NP-40 to remove the membrane. Isolated *flagella* and axonemes were quick frozen with liquid nitrogen and stored at −80° C.

TEV Protease Cleavage

To test detaching GFP from axonemes, isolated axonemes were treated with TEV protease (GenScript, Piscataway, NJ) for overnight at 4° C. and then centrifuged at 20,000×g for 20 min to collect axonemes. TEV protease treated axonemes were attached on polylysine-coated coverslips and fixed with ice-cold methanol, blocked in 5% BSA, 1% fish gelatin, and 10% normal goat serum in PBS, and incubated with mouse anti-GFP monoclonal (1:1000; Roche, Indianapolis, IN) and rabbit anti-alpha-tubulin polyclonal (1:1000; Abcam, Cambridge, MA). Axonemes were then washed with PBS and incubated with mouse-Alexa Fluor® 488 and rabbit-Alexa Fluor® 546 antibodies (1:200; Invitrogen, Waltham, MA). Samples were washed with PBS and mounted with Vectashield, then observed using a Delta Vision microscope (GE Healthcare, Chicago, IL) equipped with a 100× objective (Olympus, Tokyo, Japan). Z-stack images were obtained at 0.2-μm intervals, then deconvolved and projected with DeltaVision software (GE Healthcare).

Example 5: Experimental Design for Algae-Based Protein Production

An important challenge in biotechnology is to express proteins in active form at low cost and large scale. Experiments provided herein have identified a protein targeting system within *flagella* of green algae that can assemble proteins into high density linear arrays which can then be easily isolated from the cell without killing the cell. After array isolation, the cells can be recovered and re-used. This system will allow green algae to be used as low-cost protein array factories for large scale production. Additional experiments provide support that the system can express industrially relevant enzymes and insoluble antigens and demonstrate removal of proteins from the array and recovery of living biomass for re-use. Thus, provided herein is a flexible protein expression platform using green technology to generate soluble antigens for vaccine production as well as high density enzyme nanoarrays and liposomes for substrate channeling and in vitro conversion of products.

Much of current antigen production relies on bacterial expression systems, in which the insoluble antigen protein is purified from an inclusion body and then refolded and rendered into a soluble form. This is by no means a predictable process, creating challenges for developing new vaccines. A standardized system for isolating antigens on a protein array, in which the proteins are able to fold properly in the first place, would represent a vast improvement over current methodologies. Use of fungal rather than bacterial expression systems have helped with the solubility problem in the sense that fungal cells have a different set of chaperones, but do not address the fundamental issue that poorly soluble proteins are, by definition, hard to isolate in solution. By anchoring the proteins to an underlying protein array scaffold, the system described herein provides a quantum leap beyond existing methodologies.

In industrial enzymology, a standard procedure is "in vitro conversion" in which enzymes produced in an expression system are used to convert a product of some fermentation process into a final desired product. Because the products in question often cannot cross the cell membrane, the expressing cells must be lysed to release the enzyme, and the rest of the expression system discarded. The resulting loss of biomass is not an issue in a laboratory setting but at a large industrial scale can make the whole process prohibitively expensive. The system described herein has several advantages for large scale in vitro conversion. First, green algae can be grown in large volumes using low cost media, which is why they have been extensively explored in the biofuel sector. Second, this method allows one to isolate the protein arrays in a one-step centrifugation process that preserves the cell bodies intact, allowing them to be used for additional rounds of culture. By preserving the cellular expression system intact during array isolation, this system will provide a vastly lower cost source of enzymes compared to existing expression systems, potentially rendering many new chemical pathways economically viable.

Figure 6:
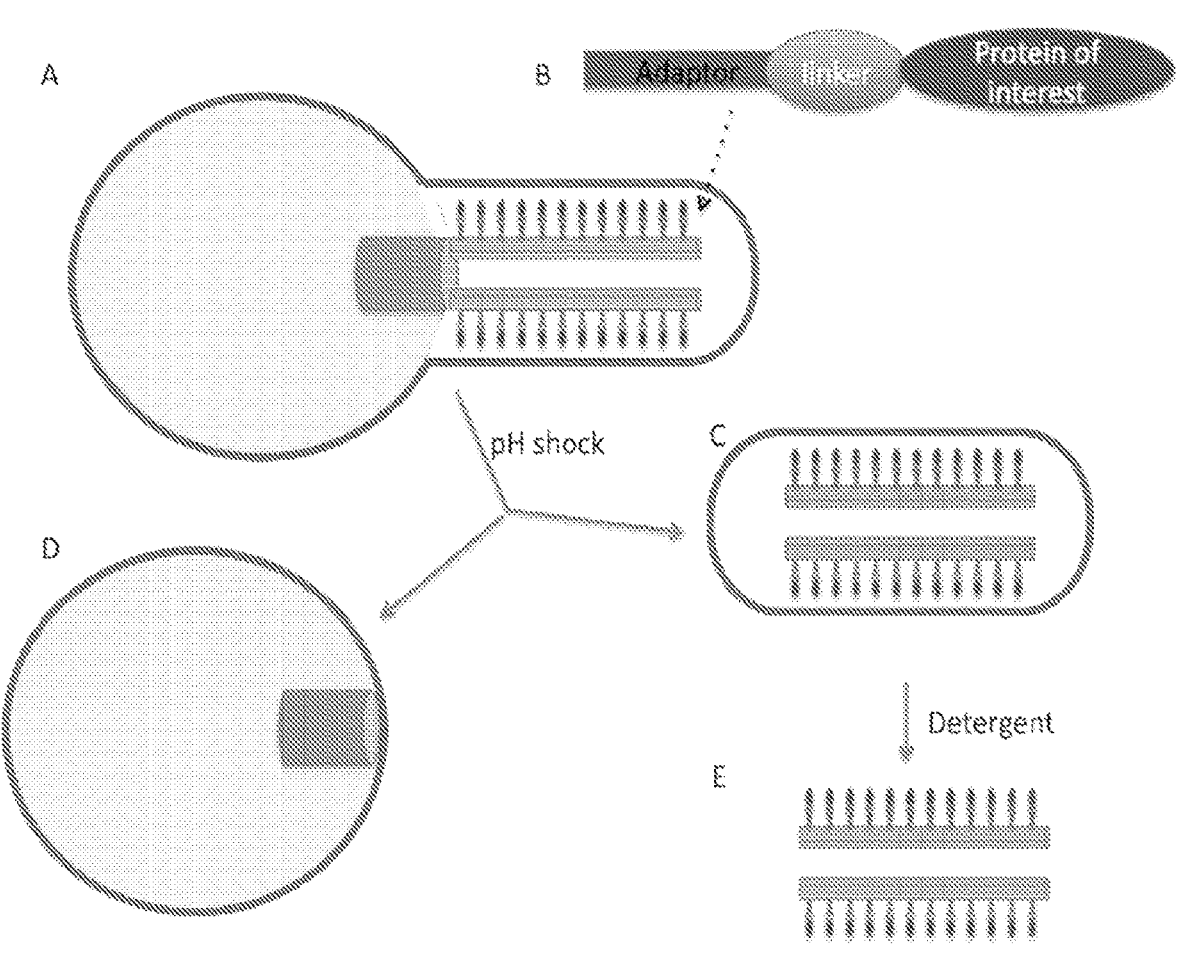
FIG. 6 is a diagram showing the harnessing of the flagellar axoneme as a biologically self-assembling protein nanoarray. A cell (A) with a protruding *flagellum*, which consists of an extension of the cell membrane overlaying a protein structural core known as the axoneme. Attached to the axoneme are numerous proteins. By fusing a protein of interest to one of the axonemal proteins (B), the axoneme protein can serve as an adaptor to attach many copies of the protein of interest into the axoneme, forming a protein array. The *flagellum* (C) can be cleanly detached from the cell body by transiently reducing the pH of the media (pH shock), which releases the cell body intact. The large cell body is easily separated from the *flagellum* and remains viable, such that biomass is completely recovered for further rounds of protein array production (D). Treatment of the isolated *flagella* with detergent leads to removal of membrane and the axoneme (E) can then be purified by a single centrifugation step. An important feature of this system is that it allows the protein array to be isolated in either a membrane-bound vesicle form (C) or a solvent exposed membrane-less form (E).
Figure 8A:
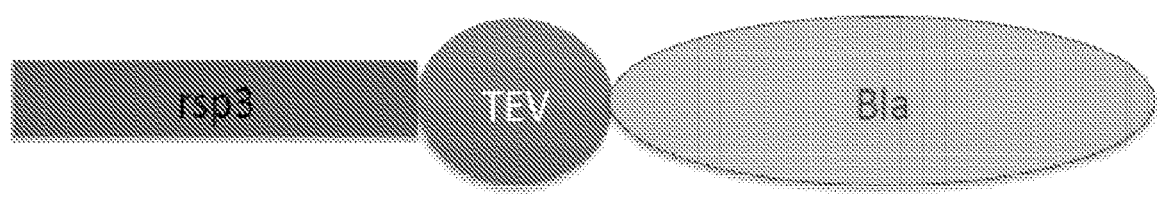
FIGS. 8A-8B present data showing that the axoneme array can incorporate functional enzymes.
Figure 8B:
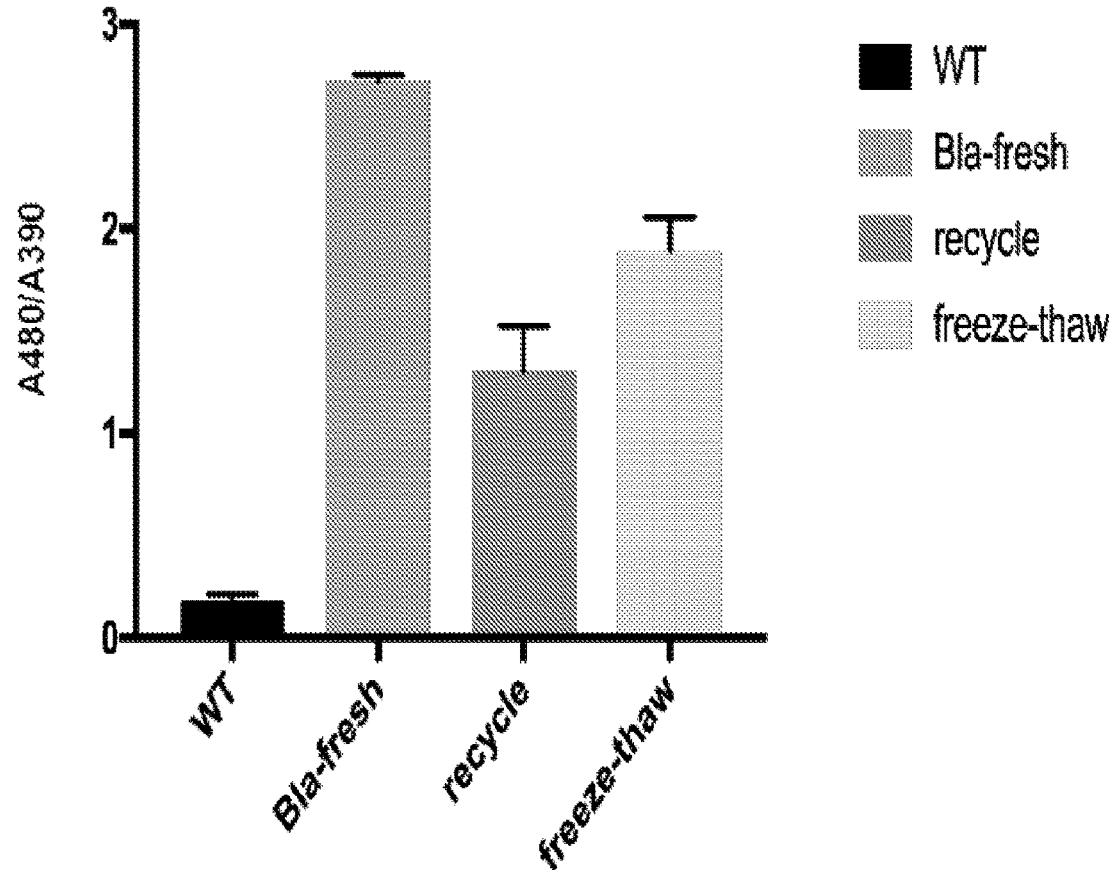
Figure 9A:
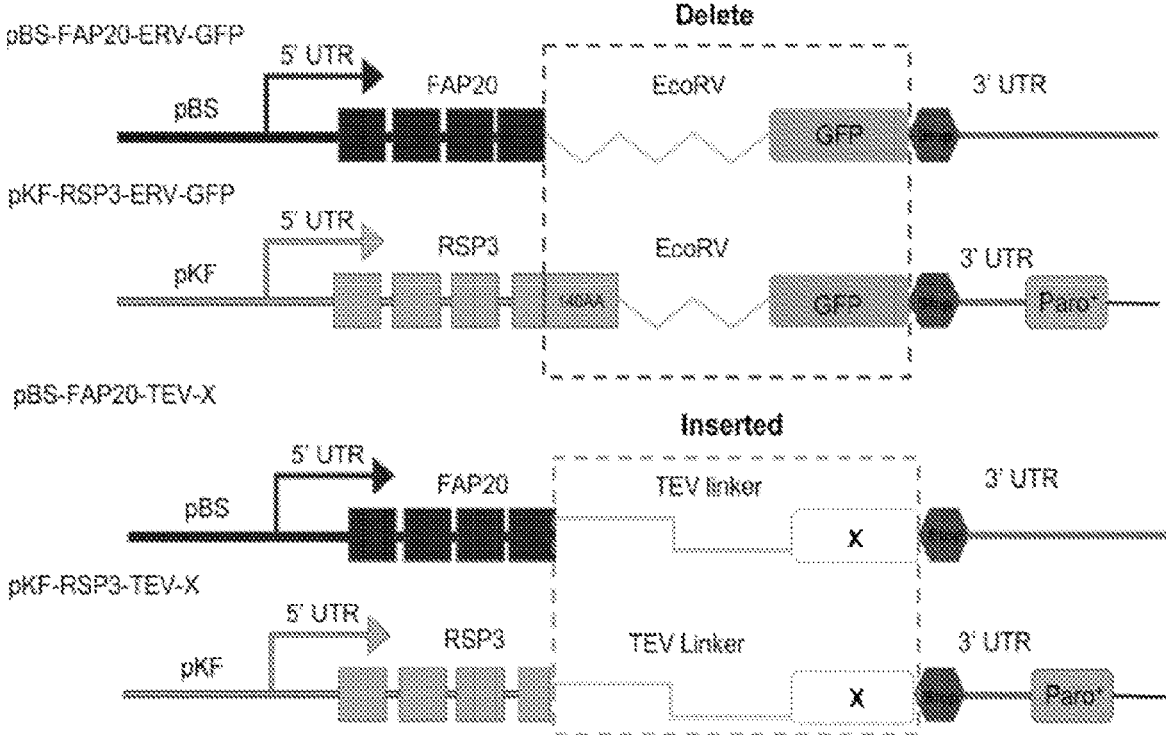
FIGS. 9A-9B convey the design of applying flagellar axoneme as a biosynthetic template.
Figure 9B:
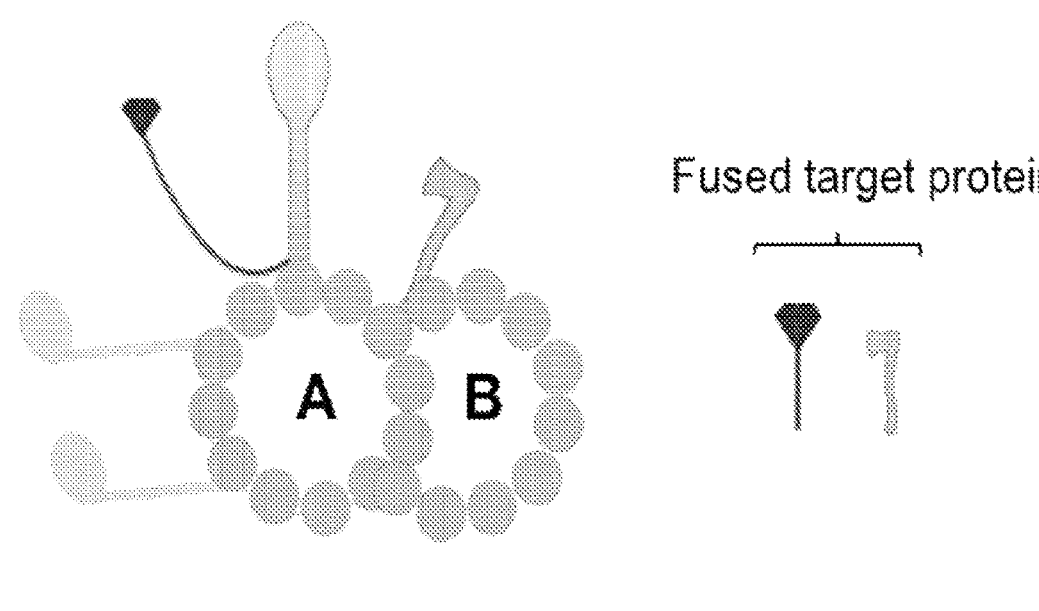
Figure 9B:
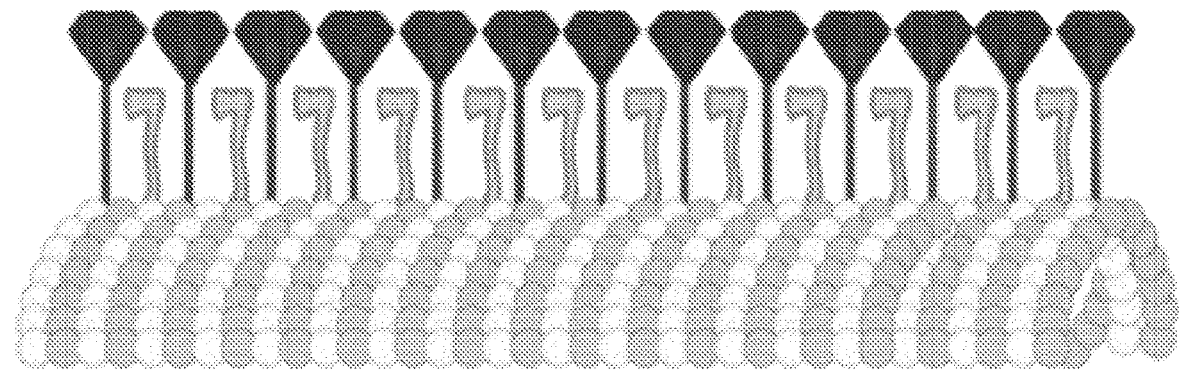
Figure 10A:
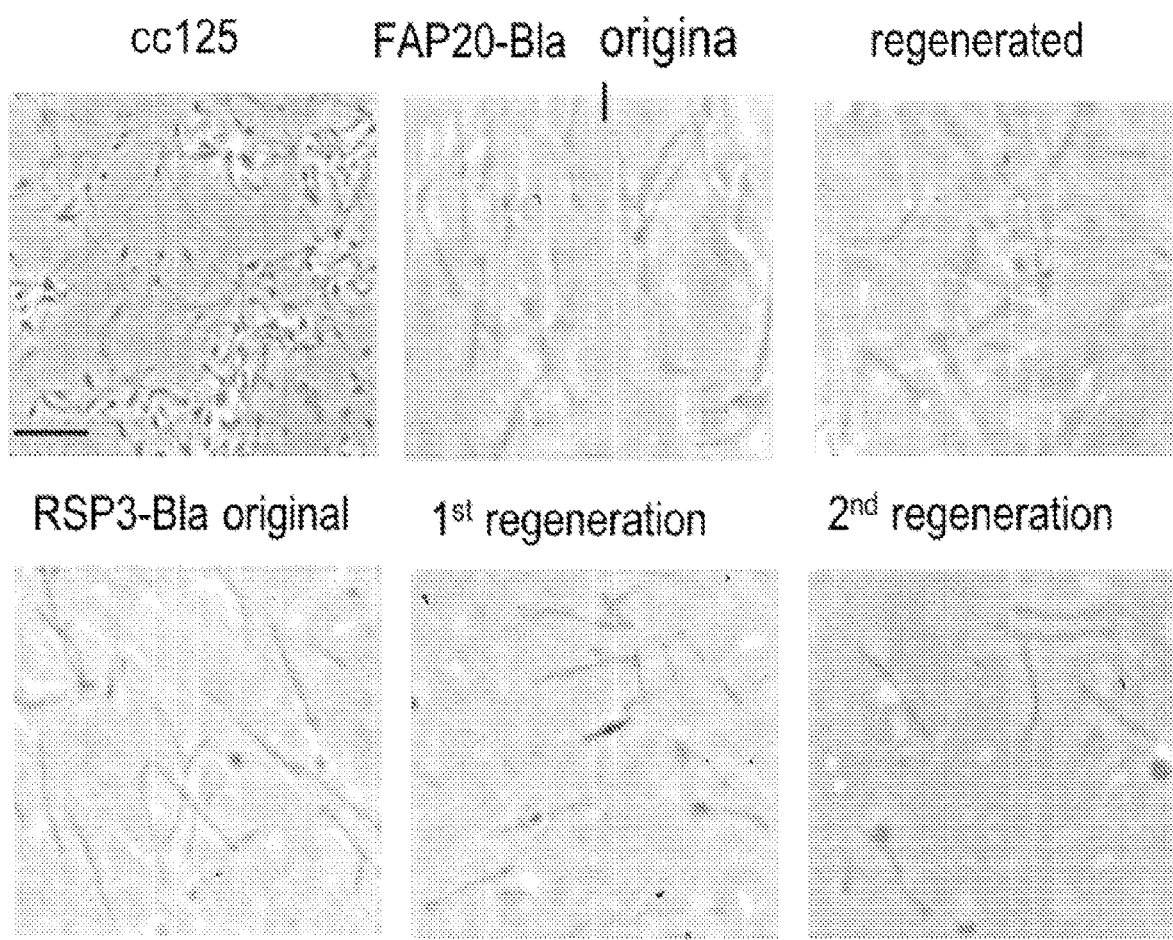
FIGS. 10A-10B present the regeneration of FAP20-Bla and RSP3-Bla *flagella*.
Figure 10B:
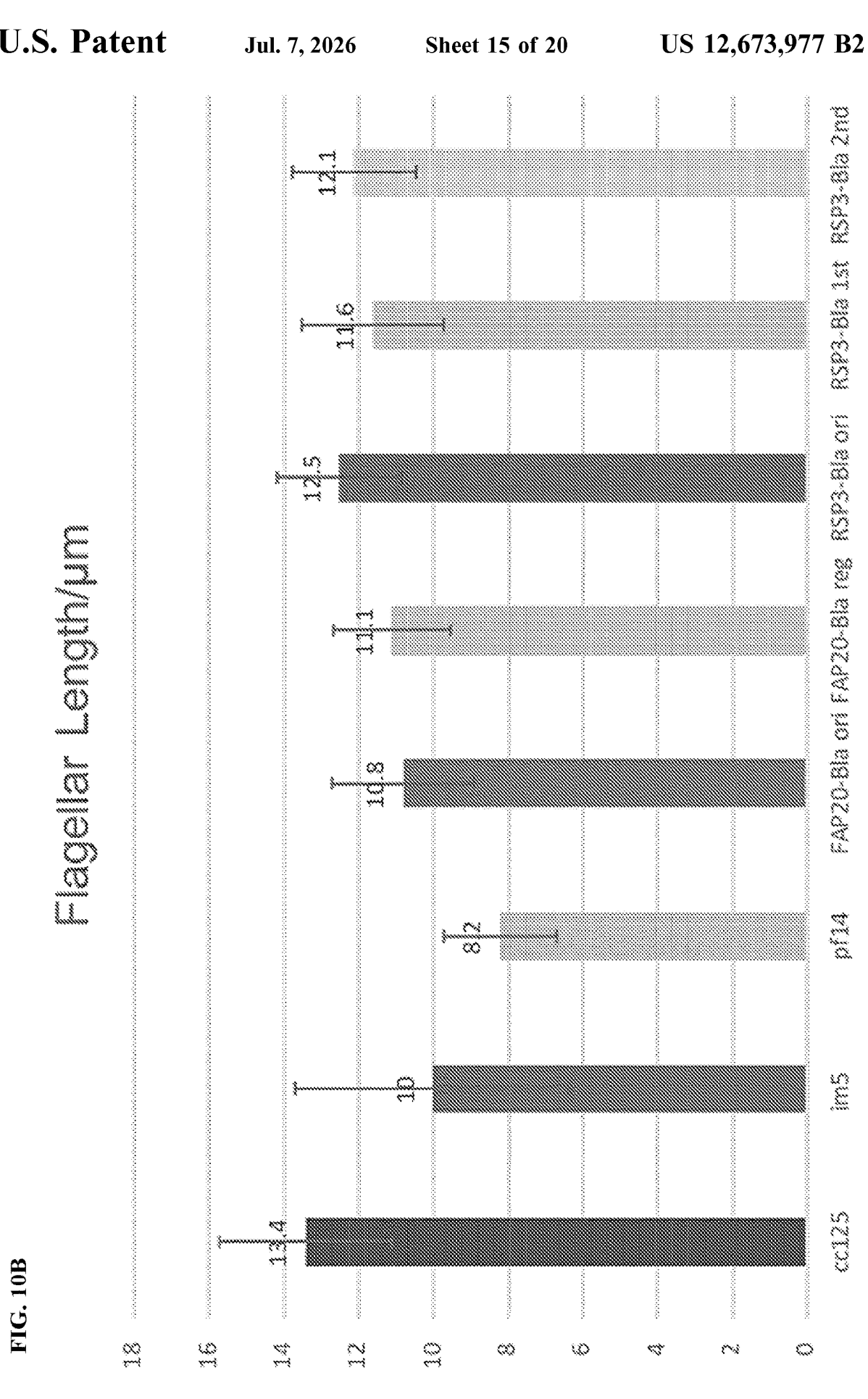
Figure 11:
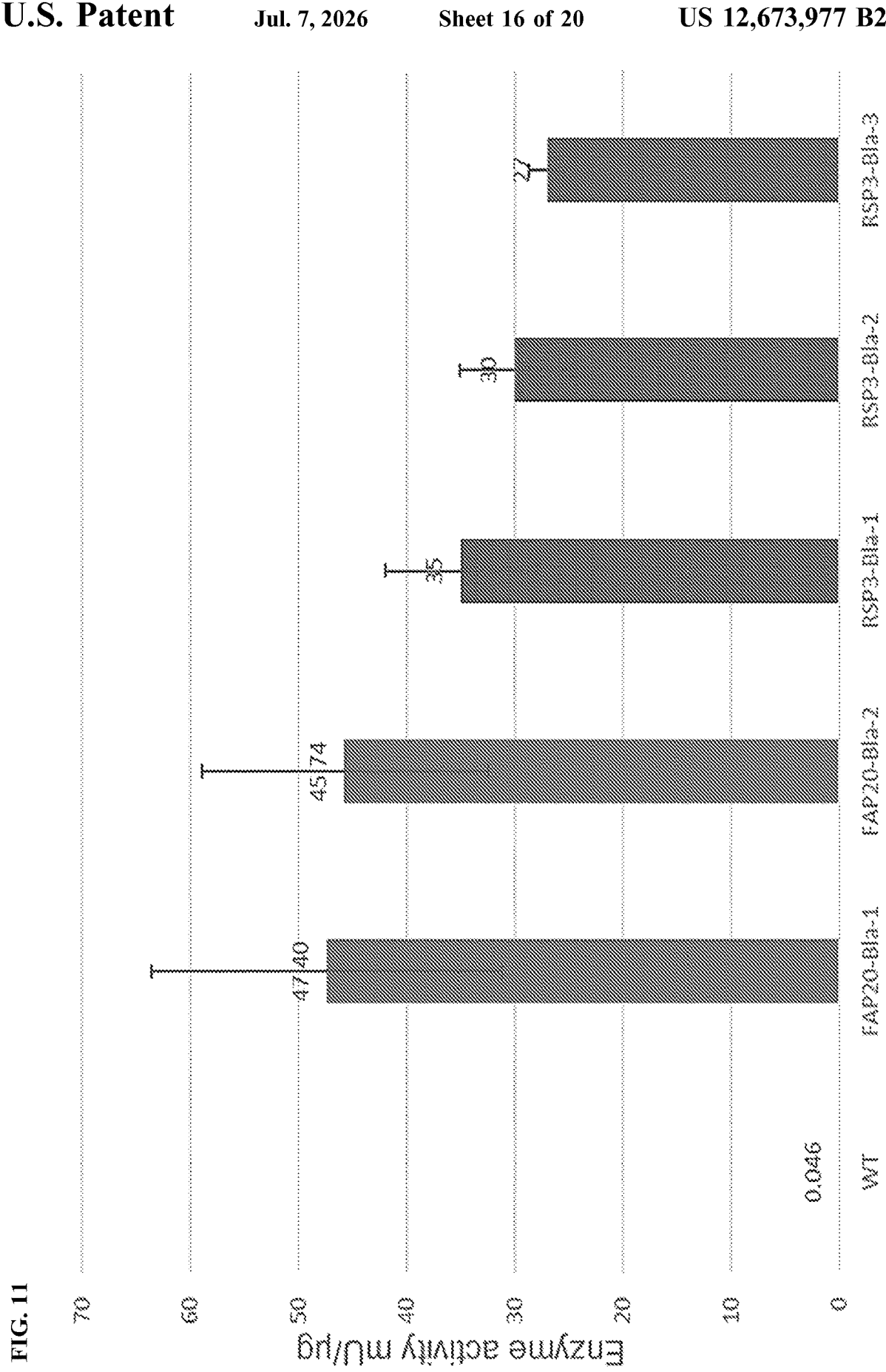
FIG. 11 is a bar graph showing the beta-lactamase activity and error bars for two replicates for each original or regenerated *flagella*. In this figure, FAP20-TEV-Bla original, regenerated *flagella*, RSP3-TEV-Bla original, first, second *flagella*, and wild type (WT) *flagella* were subjected to beta-lactamase activity assay, in which 5 μl of *flagella* from each sample were used.
Figure 12:
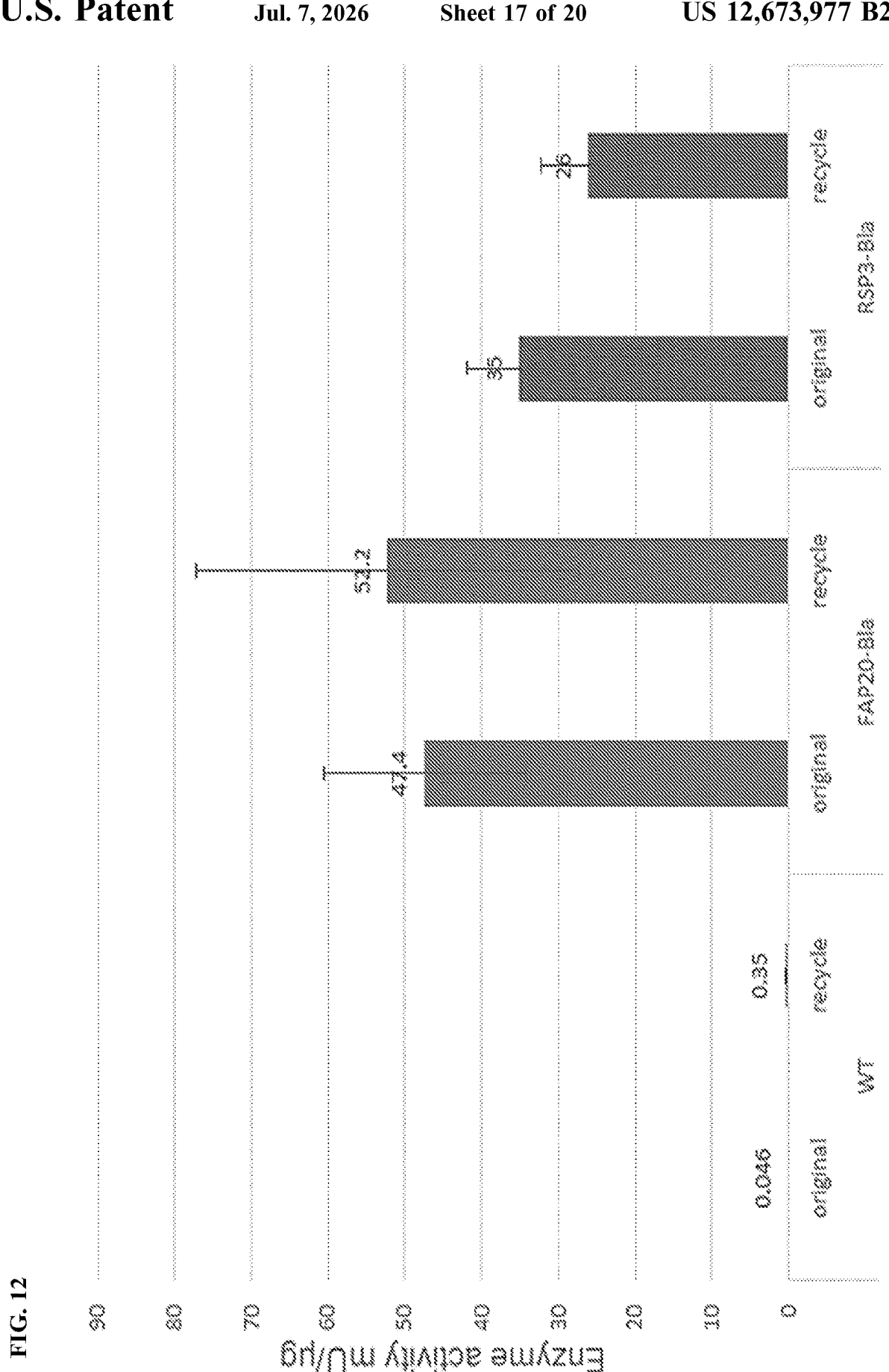
FIG. 12 is a bar graph showing the beta-lactamase activity and error bars for two replicates for original or recycled wild type (WT), FAP20-Bla, and RSP3-Bla *flagella*. For each sample, five *flagella* were incubated with 40 nM Nitrocefin in 100 μl system. After incubation, the absorbance at 490 nm was measured and the beta-lactamase activity calculated. The *flagella* from this first reaction were then purified and subjected to another reaction, as instantly described.
Figure 13:
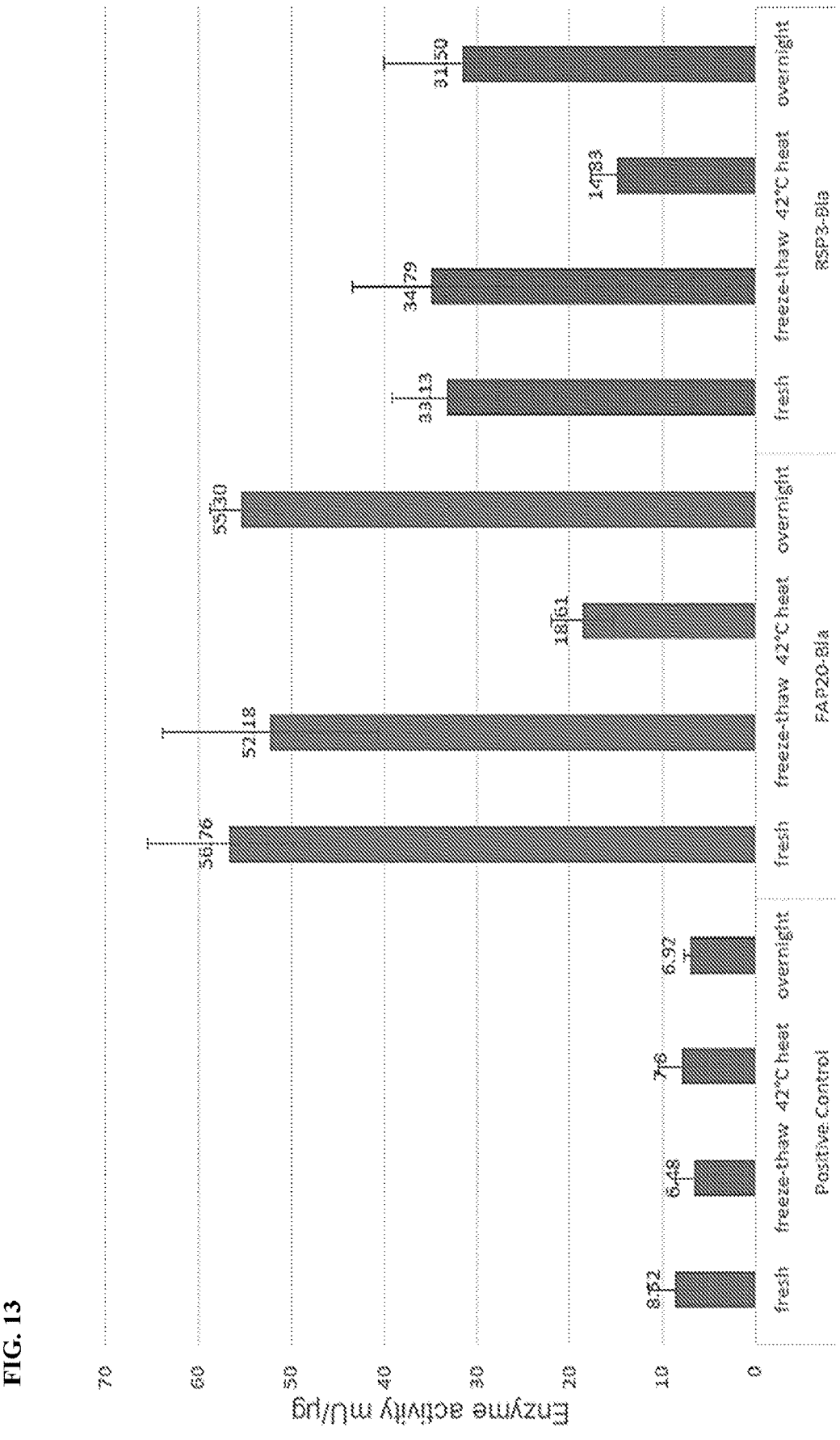
FIG. 13 is a bar graph showing the *flagella* enzymatic activity assay under different temperature treatments, for standard Beta-lactamase (Bla) enzyme, and FAP20-Bla and RSP3-Bla *flagella*. The samples were freeze-thawed four times, heated for 10 minutes at 42° C., or kept at room temperature for 48 hours. 5 μl *flagella* from each sample and treatment were subjected to beta-lactamase activity assay. The equal amount of commercial beta-lactamase enzyme was used as a positive control. Bla *flagella* enzyme was found to be resistant to the freeze-thawing treatment and durable at room temperature, but also to be heat sensitive.
Figure 14:
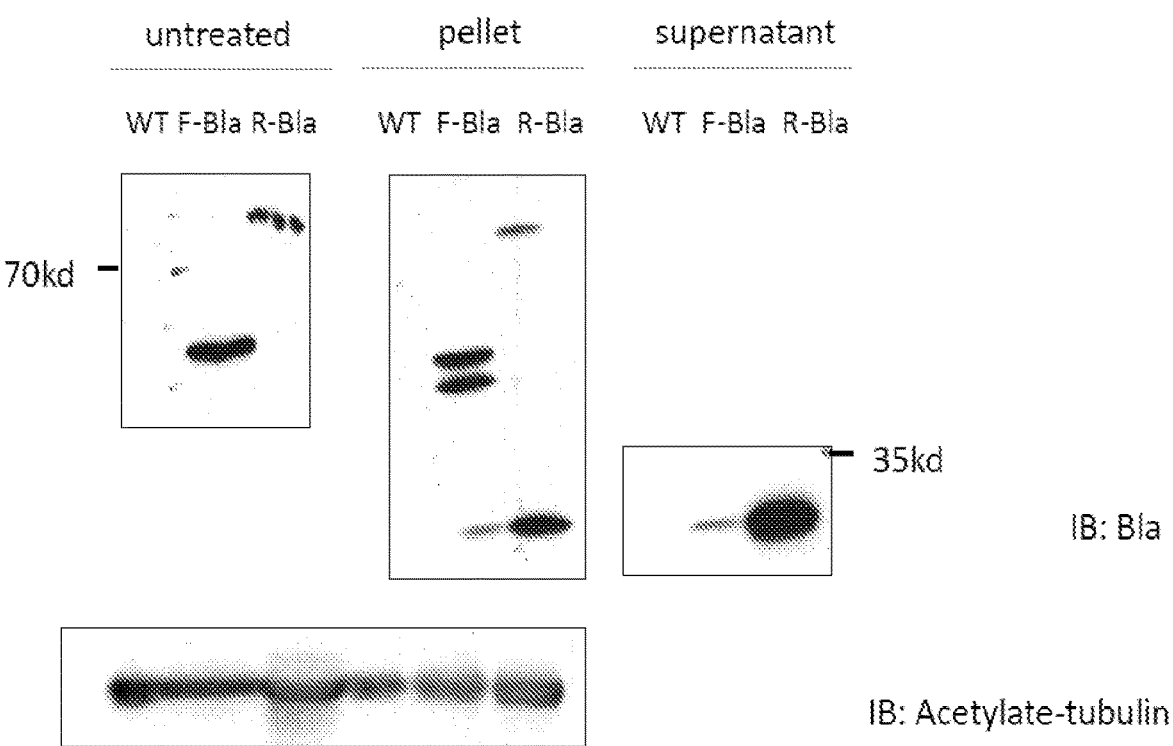
FIG. 14 presents pictures of a western blot, showing the effective cleavage of Beta-lactamase (Bla) from FAP20-Bla and RSP3-Bla axonemes, by TEV enzymatic cleavage. Wild type (WT), FAP20-Bla, and RSP3-Bla *flagella* were incubated with TEV enzyme for 2 hours at 37° C., then centrifuged at 10,000 rpm for 10 minutes to separate the axoneme pellet and supernatant. Untreated *flagella*, pellet, and supernatant were subjected to western blot and staining for Bla. The staining of acetylate-tubulin indicates equal loading of samples.
Figure 15:
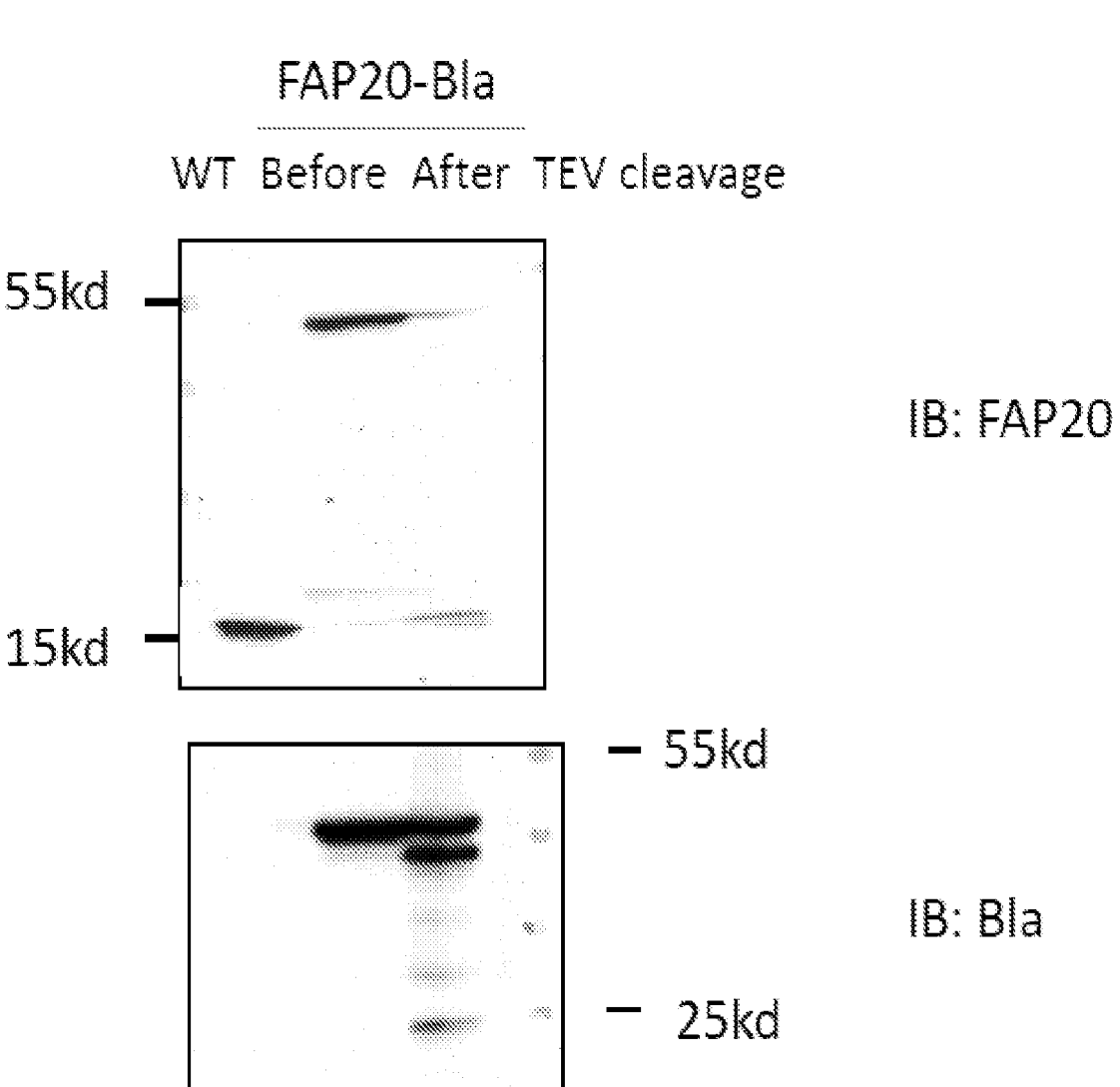
FIG. 15 presents pictures of a western blot, showing that TEV enzyme cleavage decreased the FAP20-Bla level on FAP20-Bla axonemes. For this experiment, wild type (WT), FAP20-Bla *flagella* before and after cleaved with TEV enzyme were subjected to western blot and stained for the presence of FAP20 and Beta-lactamase (Bla) proteins.

Based on initial findings that FAP20 and RSP3 can still function in fusion constructs, the idea of using the flagellar axoneme as a protein array was developed. Using GFP fusion constructs, the incorporation of both proteins into the axoneme were quantified, showing that FAP20 incorporates at a higher level and with greater spatial uniformity, making it preferable as a linking protein. Data showed that FAP20 fusion constructs remain associated with the axoneme if the *flagella* are isolated from the cell bodies in a one-step purification, that the proteins remain associated with the axoneme if the *flagella* are frozen and thawed, or if the membrane is removed, exposing the proteins to the medium (FIG. 6). These experiments showed that the axoneme can serve as a protein isolation system that is robust enough to be industrially useful. Finally, data has shown that beta lactamase can be fused to axonemal proteins, establishing the axonemal expression system for enzymes production (FIGS. 8A-B).

Demonstrate Protein Release and Biomass Recovery.

There are two requirements that would apply to any industrial application. First, is the ability of expressing cells to be recovered and re-used. Second is that the system can be used to express proteins and then recover them for various applications. Data has demonstrated that one can insert a TEV protease cleavage site between the FAP20 and heterologous proteins, so the next step was to show that we can isolate soluble GFP from axonemes and quantify the yield.

The experiments described herein tested whether *Chlamydomonas* could be utilized as a template for synthetic biology by inserting fusion proteins FAP20-TEV-Beta lactamase (Bla), These results confirmed that *flagella* are capable of assembling protein arrays. The RSP3-TEV-Bla and FAP20-TEV-Bla attached on the isolated *flagella* axoneme are enzymatically active; the *flagella*-bounded beta-lactamase was able to be recycled for reuse; repeated deflagellation and regeneration can be used to increase the yield of tagged protein. Altogether, the data indicate that *flagella* axoneme can serve as a template to synthesize biomolecules. See FIGS. 8-15.

Demonstrate Expression and Function of Industrially Relevant Enzymes

Data has shown expression of beta lactamase attached to the axonemal array, but this is just one enzyme. A series of fusion constructs will be produced in which a range of enzymes are fused to FAP20. Initial target enzymes will be retro-aldolase (K210M RA95.5-8), Kemp-eliminase HG3.17 (KE), *Aspergillus niger* monoamine oxidase variant D5 (MAO), and NADH Oxidase (NOX). The focus on these enzymes first is because their activity has been studied in a nanoarray system using a bacterial self assembling particle (Azuma et al, 2016). To note, the particle used in that study was not part of an expression system and required proteins to be added after particle assembly using chemical linkage. It is thus not a competing technology but does provide evidence that these enzymes will retain function in a high-density array. Each of these enzymes is easily assayed using standard procedures. Fusions with both FAP20 and RSP3 were tested. Successful fusion constructs will then be combined, for example KE fused to FAP20 and MAO fused to RSP3, in order to demonstrate the potential for generating multi-enzyme arrays as a prelude to testing substrate channeling.

Demonstrate Expression of Poorly Soluble Antigen Proteins

The axoneme is composed of a collection of insoluble proteins that are moved into position by a specific chaperon system. Because the axoneme is itself insoluble, it is predicted that insoluble protein domains can be added to axonemal proteins without impairing their ability to incorporate into the final structure. This will allow this system to be used as a low cost, highly efficient platform for expressing insoluble proteins, which is of particular interest for expression of antigens for vaccine production. To test this, the Trypanosome *cruzi* vaccine antigen peptides CP1 and CP2 will be utilized. These peptides are currently produced as inclusion bodies in *E. coli*, making them an ideal test-case for the strategy for expressing poorly soluble proteins. Fusion constructs encoding these chimeric antigen peptides with FAP20 will be generated, axonemes from expressing cells isolated, and probed with antibodies that recognize the properly folded antigens. Completion of this aim will prove the potential of our system for vaccine antigen production.

REFERENCES

1. Rae B D, Long B M, Badger M R, Price G D. "Functions, Compositions, and Evolution of the Two Types of Carboxysomes: Polyhedral Microcompartments That Facilitate CO2 Fixation in Cyanobacteria and Some Proteobacteria" *Microbiol. Mol Biol. Rev.* 77, 357-379. (2013)
2. Fischbach M A, Walsh C T. "Assembly-Line Enzymology for Polyketide and Nonribosomal Peptide Antibiotics: Logic, Machinery, and Mechanisms." *Chem Rev.* 106, 3468-96. (2006)
3. Giessen T W, Silver P A. "A catalytic nanoreactor based on in vivo encapsulation of multiple enzymes in an engineered protein nanocompartment." *Chembiochem* 17, 1931-35. (2016)
4. Azuma Y, Zschoche R, Tinzl M, Hilvert D. "Quantitative packaging of active enzymes into a protein cage." *Angewandte Chem. Int. Ed.* 55, 1531-1534. (2016)
5. Noree C, Sato B K, Broyer R M, Wilhelm J E. "Identification of novel filament-forming proteins in *Saccharomyces cerevisiae* and *Drosophila melanogaster.*" *J. Cell Biol.* 190, 541-51. (2010)
6. Oosawa F, Kasai M. "A theory of linear and helical aggregations of macromolecules." *J. Mol. Biol.* 4, 10-21. (1962)
7. Kawamura M, Maruyama K. "Electron microscopic particle length of F-actin polymerized in vitro." *J. Biochem.* 67, 437-57. (1970)
8. Gregoretti I V, Margolin G, Alber M S, Goodson H V. "Insights into cytoskeletal behavior from computational modeling of dynamic microtubules in a cell-like environment." *J. Cell Sci.* 119, 4781-8. (2006)
9. Janulevicius A, van Pelt J, van Ooyen A. "Compartment volume influences microtubule dynamic instability: amodel study." *Biophys. J.* 90, 788-98. (2006)
10. Katsura I. "Determination of bacteriophage lambda tail length by a protein ruler." *Nature* 327:73-75 (1987)

11. Wagner S, Sorg I, Degiacomi M, Journet L, Dai Peraro M, Cornelis G R. "The helical content of the YscPmolecular ruler determines the length of the *Yersinia* injectisome." *Mol. Microbiol.* 71, 692-701. (2009).

12. Kannegaard E, Rego E H, Shuck S, Feldman J L, Marshall W F. "Quantitative analysis and modeling of katanin function in flagellar length control." *Mol. Biol. Cell* 25, 3686-98. (2014)

13. Ludington W B, Ishikawa H, Serebrenik Y V, Ritter A, Hernandez-Lopez R A, Gunzenhauser J, Kannegaard E, Marshall W F. "A systematic comparison of mathematical models for inherent measurement of ciliary length: how a cell can measure length and volume." *Biophys. J.* 108, 1361-79. (2015)

14 Silflow, C. D., and Lefebvre, P. A. "Assembly and motility of eukaryotic *cilia* and *flagella*. Lessons from *Chlamydomonas reinhardtii.*" *Plant Physiol.* 127,1500-7. (2001)

15. McVittie, A. C. "Flagellum mutants of *Chlamydomonas reinhardtii.*" *J. Gen. Microbiol.* 71,525-540. (1972)

16. Barsel, S. E., Wexler, D. E., and Lefebvre, P. A. "Genetic analysis of long-*flagella* mutants of *Chlamydomonas reinhardtii.*" *Genetics* 118,637-48 (1988)

17. Asleson, C. M. and Lefebvre, P. A. "Genetic analysis of flagellar length control in *Chlamydomonas reinhardtii*: a new long-*flagella* locus and extragenic suppressor mutations." *Genetics* 148,693-702. (1998)

18. Kuchka, M. R., and Jarvik, J. W. "Short-*flagella* mutants of *Chlamydomonas.*" *Genetics* 115,685-691. (1987)

19. Nakamura S, Takino H, and Kojima M K. "Effect of lithium on flagellar length in *Chlamydomonas reinhardtii.*" *Cell Struct. Funct.* 12, 369-374. (1972)

20. Engel B D, Ishikawa H, Feldman J L, Wilson C W, Chuang P T, Snedecor J, Williams J, Sun Z, and Marshall, W F. "A cell-based screen for inhibitors of *flagella*-driven motility in *Chlamydomonas* reveals a novel modulator of ciliary length and retrograde actin flow." *Cytoskeleton* 68, 188-203. (2011)

21. Avasthi P, Marley A, Lin H, Gregori-Puigjane E, Shoichet B K, von Zastrow M, Marshall W F. "A chemical screen identifies class A G-protein coupled receptors as regulators of *cilia.*" *ACS Chemical. Biol.* 7, 911-9. (2012)

22. Kozminski K G, Johnson K A, Forscher P, Rosenbaum J L. "A motility in the eukaryotic *flagellum* unrelated to flagellar beating." *Proc. Natl. Acad. Sci. U.S.A.* 90, 5519-23. (1993)

23. Ishikawa H, Marshall W F. "Ciliogenesis: building the cell's antenna." *Nat. Rev. Cell Mol. Biol.* 12, 222-234. (2011)

24. Taschner M, Lorentzen E. "The intraflagellar transport machinery." *Cold Spring Harbor Persp Biol.* 8, a028092 (2016)

25. Oda T, Yanagisawa H, Kamiya R, Kikkawa M. "A molecular ruler determines the repeat length in eukaryotic *cilia* and *flagella.*" *Science* 346, 857-60. (2014)

26. U.S. Department of Energy. *National Algal Biofuels Technology Roadmap.* U.S. DOE Office of Energy Efficiency and Renewable Energy, Biomass Program (2010)

27. Ahmed N T, Gao C, Lucker B F, Cole D G, Mitchell D R. "ODA16 aids axonemal outer row dynein assembly through an interaction with the intraflagellar transport machinery." *J. Cell Biol.* 183, 313-22. (2008)

28. Ishikawa H, Ide T, Yagi T, Jiang X, Hirono M, Sasaki H, Yanagisawa H, Wemmer K A, Stainier D Y, Qin H, Kamiya R, Marshall W F. "TTC26/DYF13 is an intraflagellar transport protein required for transport of motility-related proteins into *flagella.*" *eLife* 3, e01566 (2014)

29. Nachury M V. "The molecular machines that traffic signaling receptors into and out of *cilia.*" *Curr. Opin. Cell Biol.* 51, 124-131. (2018)

30. Craige B, Brown J M, Witman G B. "Isolation of *Chlamydomonas flagella.*" *Curr. Protoc. Cell Biol.* 3.41, 1-19. (2013)

31. Curry A M, Rosenbaum J L. "Flagellar radial spoke: a model molecular genetic system for studying organelle assembly." *Cell Motil. Cytoskel.* 24, 224-32. (1993)

32. Luck D, Piperno G, Ramanis Z, Huang B. "Flagellar mutants of *Chlamydomonas*: studies of radial spoke-defective strains by dikaryon and revertant analysis." *Proc. Natl. Acad. Sci. U.S.A.* 74, 3456-3460. (1977)

33. Yanagisawa H A, Mathis G, Oda T, Hirono M, Richey E A, Ishikawa H, Marshall W F, Kikkawa M, and Qin H. "FAP20 is an inner junction protein of doublet microtubules essential for both the planar asymmetrical waveform and stability of *flagella* in *Chlamydomonas.*" *Mol. Biol. Cell* 25, 1472-83. (2014)

34. Quarmby, L. M. and Hartzell, H. C. "Two distinct, calcium-mediated, signal transduction pathways can trigger deflagellation in *Chlamydomonas reinhardtii.*" *J. Cell Biol.* 124, 807-15. (1994)

35. Dutta S. Avasthi P. "Flagellar Synchronization Is a Simple Alternative to Cell Cycle Synchronization for Ciliary and Flagellar Studies." *mSphere* 2, e00003-17. (2017)

P. Embodiments

P Embodiment 1. An algal cell comprising: a nucleic acid encoding a fusion protein, wherein the fusion protein comprises an axonemal protein linked to a heterologous protein through an enzyme cleavable linker, and wherein the fusion protein provides axonemal function to the algal cell.

P Embodiment 2. The algal cell of P Embodiment 1, wherein the algal cell is *Chlamydomonas.*

P Embodiment 3. The algal cell of P Embodiment 2, wherein the algal cell is *Chlamydomonas reinhardtii.*

P Embodiment 4. The algal cell of any one of P Embodiments 1-3, wherein the heterologous protein is an enzyme.

P Embodiment 5. The algal cell of P Embodiment 4, wherein the enzyme is selected from retro-aldolase (K210M RA95.5-8). Kemp-eliminase HG3.17 (KE), *Aspergillus niger* monoamine oxidase variant D5 (MAO), NADH Oxidase (NOX), and beta-lactamase.

P Embodiment 6. The algal cell of any one of P Embodiments 1-5, wherein the axonemal protein is selected from FAP20, RSP3, IFT20, and DRC4.

P Embodiment 7. The algal cell of any one of P Embodiments 1-6, wherein the enzyme cleavable linker comprises a Tobacco Etch Virus (TEV) protease cleavage site.

P Embodiment 8. A plurality of algal cells wherein each algal cell comprises: a nucleic acid encoding a fusion protein, wherein the fusion protein comprises an axonemal protein linked to a heterologous protein through an enzyme cleavable linker, and wherein the fusion protein provides axonemal function to the algal cell.

P Embodiment 9. The plurality of algal cells of P Embodiment 8, wherein the plurality of algal cells are *Chlamydomonas.*

P Embodiment 10. The plurality of algal cells of P Embodiment 9, wherein the plurality of algal cells are *Chlamydomonas reinhardtii.*

P Embodiment 11. The plurality of algal cells of any one of P Embodiments 8-10, wherein the heterologous protein is an enzyme.

P Embodiment 12. The plurality of algal cell of P Embodiment 11, wherein the enzyme is selected from retro-aldolase (K210M RA95.5-8), Kemp-eliminase HG3.17 (KE). *Aspergillus niger* monoamine oxidase variant D5 (MAO), and NADH Oxidase (NOX), and beta-lactamase.

P Embodiment 13. The plurality of algal cells of any one of P Embodiments 8-12, wherein the axonemal protein is selected from FAP20, RSP3, IFT20, and DRC4.

P Embodiment 14. The plurality of algal cells of any one of P Embodiments 8-13, wherein the cleavable linker comprises a Tobacco Etch Virus (TEV) protease cleavage site.

P Embodiment 15. A recombinant protein comprising:
a. an algal axonemal protein; and
b. a heterologous protein; and
wherein the axonemal protein is linked to the heterologous protein through an enzyme cleavable linker; and
wherein the recombinant protein provides axonemal function to the algal cell.

P Embodiment 16. The recombinant protein of P Embodiment 15, wherein the axonemal protein is selected from FAP20, RSP3, IFT20, and DRC4.

P Embodiment 17. The recombinant protein of any one of P Embodiments 15-16, wherein the axonemal protein is a *Chlamydomonas* axonemal protein.

P Embodiment 18. The recombinant protein of P Embodiment 17, wherein the axonemal protein is a *Chlamydomonas reinhardtii* axonemal protein.

P Embodiment 19. The recombinant protein of any one of P Embodiments 15-18, wherein the heterologous protein is an enzyme.

P Embodiment 20. The recombinant protein of P Embodiment 19, wherein the enzyme is selected from retro-aldolase (K210M RA95.5-8), Kemp-eliminase HG3.17 (KE), *Aspergillus niger* monoamine oxidase variant D5 (MAO), and NADH Oxidase (NOX), and beta-lactamase.

P Embodiment 21. The recombinant protein of any one of P Embodiments 15-20, wherein the enzyme cleavable linker comprises a Tobacco Etch Virus (TEV) protease cleavage site.

P Embodiment 22. An isolated nucleic acid encoding the fusion or recombinant protein of any one of P Embodiments 1-21.

P Embodiment 23. An expression vector comprising the nucleic acid of P Embodiment 22.

P Embodiment 24. An isolated algal *flagella* comprising: a flagellar membrane encompassing an axoneme, wherein said axoneme comprises a fusion protein, wherein the fusion protein comprises an algal axonemal protein linked to a heterologous protein, and wherein the fusion protein provides axonemal function to the algal cell.

P Embodiment 25. The isolated algal *flagella* of P Embodiment 24, wherein the algal axonemal protein is selected from FAP20, RSP3, IFT20, and DRC4.

P Embodiment 26. The isolated algal *flagella* of any one of P Embodiments 24-25, wherein the algal axonemal protein is a *Chlamydomonas* axonemal protein.

P Embodiment 27. The isolated algal *flagella* of any one of P Embodiments 24-26, wherein the algal axonemal protein is a *Chlamydomonas reinhardtii* axonemal protein.

P Embodiment 28. The isolated algal *flagella* of any one of P Embodiments 24-27, wherein the heterologous protein is an enzyme.

P Embodiment 29. The isolated algal *flagella* of P Embodiment 28, wherein the enzyme is selected from retro-aldolase (K210M RA95.5-8), Kemp-eliminase HG3.17

(KE), *Aspergillus niger* monoamine oxidase variant D5 (MAO), and NADH Oxidase (NOX), and beta-lactamase.

P Embodiment 30. An isolated axoneme comprising a fusion protein, wherein said fusion protein comprises an algal axonemal protein linked to a heterologous protein, and wherein the fusion protein provides axonemal function to the algal cell.

P Embodiment 31. The isolated axoneme of P Embodiment 30, wherein the algal axonemal protein is selected from FAP20, RSP3, IFT20, and DRC4.

P Embodiment 32. The isolated axoneme of any one of P Embodiments 30-31, wherein the algal axonemal protein is a *Chlamydomonas* axonemal protein.

P Embodiment 33. The isolated algal *flagella* of any one of P Embodiments 30-32, wherein the algal axonemal protein is a *Chlamydomonas reinhardtii* axonemal protein.

P Embodiment 34. The isolated axoneme of any one of P Embodiments 30-33, wherein the heterologous protein is an enzyme.

P Embodiment 35. The isolated axoneme of P Embodiment 34, wherein the enzyme is selected from retro-aldolase (K210M RA95.5-8), Kemp-eliminase HG3.17 (KE), *Aspergillus niger* monoamine oxidase variant D5 (MAO), and NADH Oxidase (NOX), and beta-lactamase.

P Embodiment 36. A plurality of axonemes wherein each of said plurality of axonemes comprise a fusion protein, wherein said fusion protein comprises an algal axonemal protein linked to a heterologous protein, and wherein the fusion protein provides axonemal function to the algal cell.

P Embodiment 37. The plurality of axonemes of P Embodiment 36, wherein the algal axonemal protein is selected from FAP20, RSP3, IFT20, and DRC4.

P Embodiment 38. The plurality of axonemes of any one of P Embodiments 36-37, wherein the algal axonemal protein is a *Chlamydomonas* axonemal protein.

P Embodiment 39. The plurality of axonemes of any one of P Embodiments 36-38, wherein the algal axonemal protein is a *Chlamydomonas reinhardtii* axonemal protein.

P Embodiment 40. The plurality of axonemes of any one of P Embodiments 36-39, wherein the heterologous protein is an enzyme.

P Embodiment 41. The plurality of axonemes of P Embodiment 40, wherein the enzyme is selected from retro-aldolase (K210M RA95.5-8), Kemp-eliminase HG3.17 (KE), *Aspergillus niger* monoamine oxidase variant D5 (MAO), and NADH Oxidase (NOX), and beta-lactamase.

P Embodiment 42. The plurality of axonemes of any one of P Embodiments 36-41, wherein the plurality of axonemes are attached to a solid support.

P Embodiment 43. The plurality of axonemes of any one of P Embodiments 36-42, wherein said heterologous protein is capable of binding to a biomolecule, a cell, or a multicellular organism.

P Embodiment 44. The plurality of axonemes of P Embodiment 43, wherein said heterologous protein is capable of binding to one or more of DNA, RNA, a vector, a virus vector, a peptide, a protein, an antibody, an antigen, a tissue factor, a lipid, a fatty acid, a steroid, a neurotransmitter, a vitamin, a toxin, a mineral, an inorganic ion, a free radical, a carbohydrate, a small molecule, an exons, a metabolite, a chromosome, a bacterium, a fungi, and/or a protozoa.

P Embodiment 45. The plurality of axonemes of any one of P Embodiments 36-44, wherein said plurality of axonemes form part of a biosensor, wherein the binding of said heterologous protein to said biomolecule, cell, or multicellular organism produces a detectable signal.

P Embodiment 46. The plurality of axonemes of P Embodiment 45, wherein the detectable signal is selected from fluorescence, kinetic change of concentration, change of pH, change of visible color, and an electric potential change.

P Embodiment 47. A method of isolating a heterologous protein comprising:

a. expressing a fusion protein in an algal *flagella* of an algal cell, wherein the fusion protein comprises an algal axonemal protein linked to a heterologous protein through a cleavable linker;

b. separating said fusion protein from said algal *flagella*; and c. contacting said fusion protein with an enzyme thereby isolating said heterologous protein.

P Embodiment 48. The method of P Embodiment 47, wherein separating comprises detaching the algal *flagella* from the algal cells thereby forming a detached *flagella*.

P Embodiment 49. The method of P Embodiment 48, wherein detaching the algal *flagella* comprises exposing the algal cell to pH shock and centrifugation to produce purified *flagella*.

P Embodiment 50. The method of any one of P Embodiments 47-49, wherein said separating further comprises isolating an axoneme from said detached *flagella*.

P Embodiment 51. The method of any one of P Embodiments 47-50, wherein the algal axonemal protein is selected from FAP20, RSP3, IFT20, and DRC4.

P Embodiment 52. The method of any one of P Embodiments 47-51, wherein the algal axonemal protein is a *Chlamydomonas* axonemal protein.

P Embodiment 53. The method of any one of P Embodiments 47-52, wherein the algal axonemal protein is a *Chlamydomonas reinhardtii* axonemal protein.

P Embodiment 54. The method of any one of P Embodiments 47-53, wherein the heterologous protein is an enzyme.

P Embodiment 55. The method of P Embodiment 54, wherein the enzyme is selected from retro-aldolase (K210M RA95.5-8), Kemp-eliminase HG3.17 (KE), *Aspergillus niger* monoamine oxidase variant D5 (MAO), and NADH Oxidase (NOX), and beta-lactamase.

What is claimed is:

1. An algal cell comprising: a nucleic acid encoding a fusion protein, wherein the fusion protein comprises an axonemal protein linked to a heterologous protein through an enzyme cleavable linker, wherein said axonemal protein is FAP20, and wherein the heterologous protein is an enzyme.

2. The algal cell of claim 1, wherein the enzyme is selected from retro-aldolase, Kemp-eliminase HG3.17 (KE), *Aspergillus niger* monoamine oxidase variant D5 (MAO), NADH oxidase (NOX), and beta-lactamase.

3. A plurality of algal cells wherein each algal cell comprises: a nucleic acid encoding a fusion protein, wherein the fusion protein comprises an axonemal protein linked to a heterologous protein through an enzyme cleavable linker, wherein said axonemal protein is FAP20, and wherein the heterologous protein is an enzyme.

4. The plurality of algal cell of claim 3, wherein the enzyme is selected from retro-aldolase, Kemp-eliminase HG3.17 (KE), *Aspergillus niger* monoamine oxidase variant D5 (MAO), NADH oxidase (NOX), and beta-lactamase.

5. A recombinant protein comprising:

a. an algal axonemal protein, and b. a heterologous protein;

wherein the axonemal protein is linked to the heterologous protein through an enzyme cleavable linker; wherein said axonemal protein is FAP20; and wherein the heterologous protein is an enzyme.

6. The recombinant protein of claim 5, wherein the enzyme is selected from retro-aldolase, Kemp-eliminase HG3.1 7 (KE), *Aspergillus niger* monoamine oxidase variant D5 (MAO), NADH oxidase (NOX), and beta-lactamase.

7. An isolated nucleic acid encoding the recombinant protein of claim 5.

\* \* \* \* \*